US 6,595,948 B2

(12) United States Patent
Suzuki et al.

(10) Patent No.: US 6,595,948 B2
(45) Date of Patent: Jul. 22, 2003

(54) PERITONEAL DIALYSIS APPARATUS

(75) Inventors: Minoru Suzuki, Fuji (JP); Akira Minagawa, Fuji (JP); Hironobu Suzuki, Fuji (JP); Jun Tsubota, Tokyo (JP); Kazuhiko Hirota, Nagano (JP); Yoshikazu Makiuchi, Nagano (JP)

(73) Assignee: Terumo Kabushiki Kaisha, Tokyo (JP)

( * ) Notice: Subject to any disclaimer, the term of this patent is extended or adjusted under 35 U.S.C. 154(b) by 22 days.

(21) Appl. No.: 09/969,607

(22) Filed: Oct. 4, 2001

(65) Prior Publication Data

US 2002/0045851 A1 Apr. 18, 2002

(30) Foreign Application Priority Data

Oct. 4, 2000 (JP) .................................... 2000-305460
Jun. 19, 2001 (JP) .................................... 2001-185327
Jun. 19, 2001 (JP) .................................... 2001-185383

(51) Int. Cl.[7] ................................................ A61M 1/00
(52) U.S. Cl. ........................................................ 604/29
(58) Field of Search .............................. 604/28, 29, 30, 604/132, 141; 210/646, 650, 180, 252, 258; 417/395; 128/DIG. 12, DIG. 13

(56) References Cited

U.S. PATENT DOCUMENTS 5,350,357 A    9/1994  Kamen et al.
5,474,683 A  * 12/1995 Bryant et al. ............... 210/646
5,628,908 A  *  5/1997 Kamen et al. .............. 210/646
5,863,421 A  *  1/1999 Peter, Jr. et al. ............ 210/134
5,938,634 A  *  8/1999 Packard ....................... 604/29

FOREIGN PATENT DOCUMENTS

EP           0 956 876 A        11/1999

* cited by examiner

*Primary Examiner*—Sharon Kennedy
(74) *Attorney, Agent, or Firm*—Burns, Doane, Swecker & Mathis, LLP

(57) ABSTRACT

The invention aims to provide a compact peritoneal dialysis apparatus using a disposable cassette integrally formed with a diaphragm and heating portion, in which a flow path can be switched quietly and a heating ability is high. By using a disposable cassette (8) integrally formed with a diaphragm, heating portion, and flow path switching portion, a predetermined amount of dialysis fluid is heated to a predetermined temperature with the heating portion. Clamps (111–118) for opening/closing a flow path switching portion are provided in order to form flow paths through which the heated peritoneal dialysis fluid is distributed into the peritoneal cavity of a patient almost continuously and is sucked and drained from the peritoneal cavity of the patient. The invention also aims to provide a peritoneal dialysis apparatus with which automatic dialysis treatment can be performed by the patient himself and the operation procedures of which are very clear and easy to understand, so treatment can be performed with optimal conditions, and even if a trouble should occur, it can be coped with easily.

19 Claims, 27 Drawing Sheets

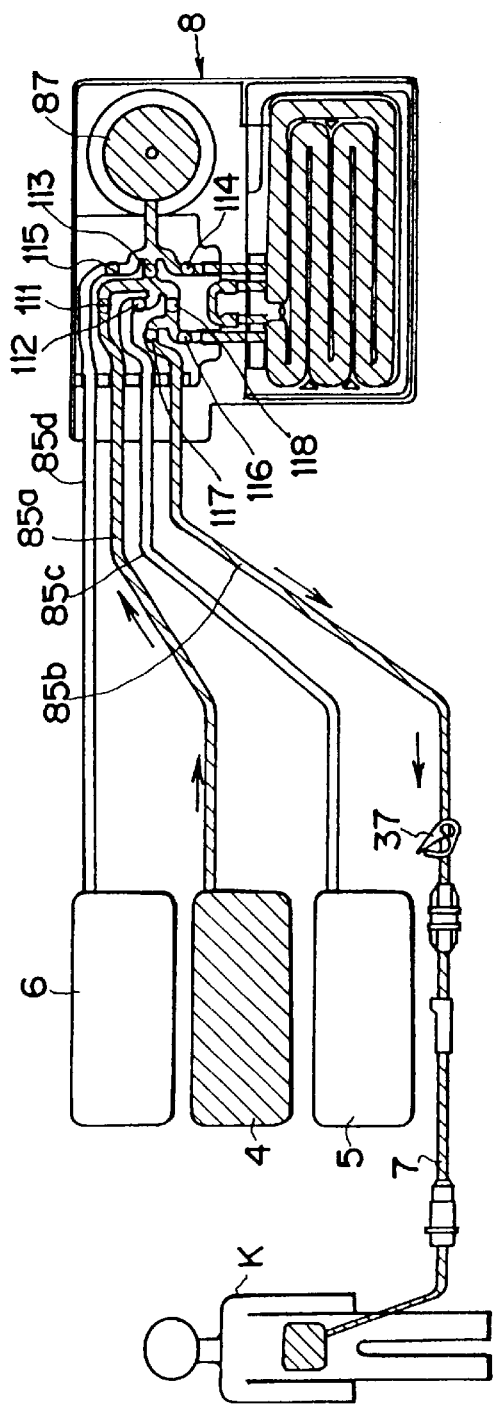
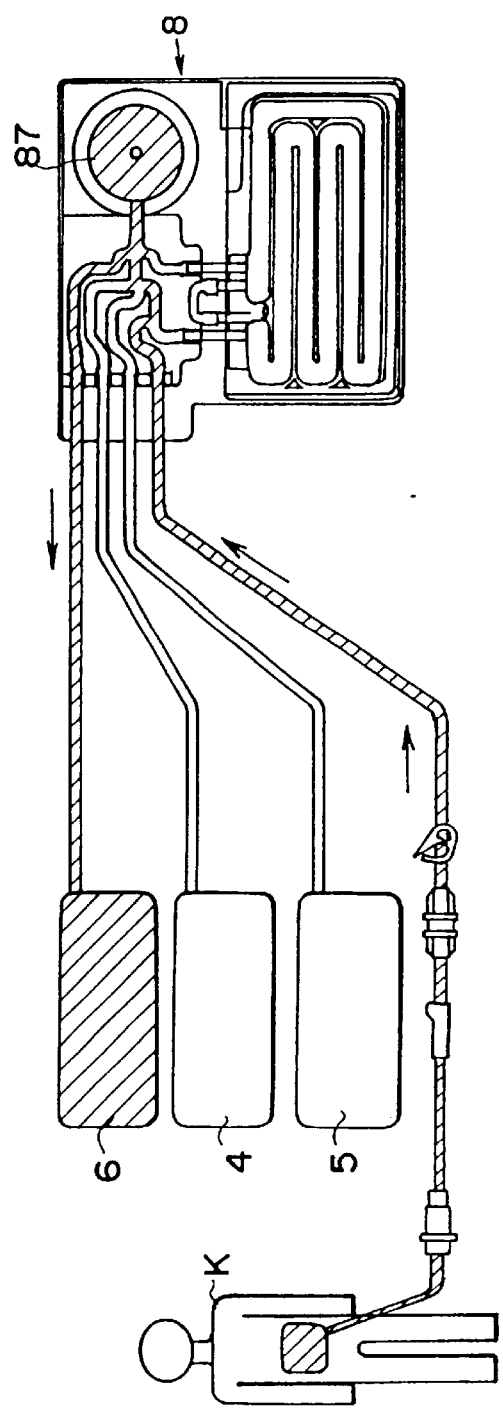
FIG. 8A
FIG. 8B

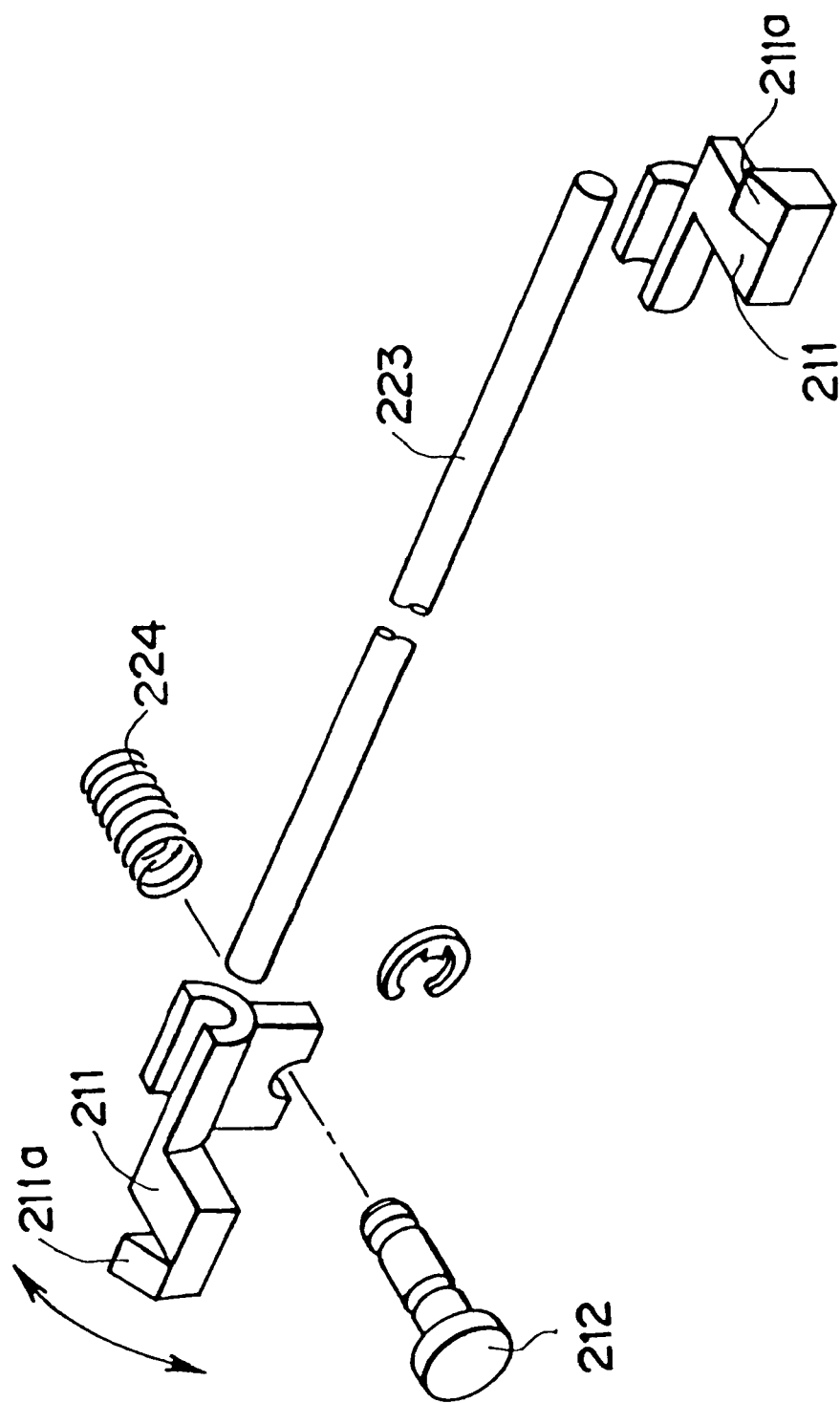

FIG. 22

23

500: TAROMU

501

502: TESTING
▲ NOTE
· PERFORM TREATMENT AT BRIGHT, CLEAN PLACE.
· DO WASH YOUR HANDS.

FOLLOW UP PREPARATION OF ENVIRONMENT WITH VOICE GUIDE

503

| TREATMENT PATTERN | NPD/CCPD | DIALYSIS TIME 7 HOURS 37 MINUTES |
| INITIAL AMOUNT OF DRAINED FLUID | 0mL | |
| AMOUNT OF INFUSED FLUID | 2000mL | PLANNED END TIME 5:37 AM, MARCH 17 |
| STAY TIME | 1 HOUR 10 MINUTES | |
| NUMBER OF CYCLES | 5 | |
| FINAL SHOT AMOUNT OF INFUSED FLUID | 0mL | TOTAL AMOUNT OF DIALYSIS FLUID 11000mL |
| FINAL CONCENTRATION ALTERED ? | NO | |

ALTER 504   TREATMENT RECORD 505   NEXT 506

FIG. 25

FROM 508
↓

523 — GUIDE  CONNECT DIALYSIS FLUID.
1. TAKE CONNECTING PORTION TO HOLDER
2. CONNECT TO DIALYSIS FLUID
3. CONNECT TO FLUID TANK
4. OPEN WHITE CLAMP
5. CHECK ALL CONNECTIONS

524 — CHECK SETTING  WHEN COMPLETED ▶ NEXT

↓

PLEASE WAIT

525

↓

526 — GUIDE  CONNECT DIALYSIS FLUID.
1. TAKE CONNECTING PORTION TO HOLDER
2. CONNECT TO DIALYSIS FLUID
3. CONNECT TO FLUID TANK
4. OPEN WHITE CLAMP
5. CHECK ALL CONNECTIONS

527 — CHECK SETTING  WHEN COMPLETED ▶ NEXT

↓

SELECT PROCEDURE YOU WANT TO SEE.  RETURN
1. TAKE CONNECTING PORTION TO HOLDER
2. CONNECT TO DIALYSIS FLUID
3. CONNECT TO FLUID TANK
4. OPEN WHITE CLAMP
5. CHECK ALL CONNECTIONS

▼ ▲                              CHECKED 530                              529

528

PERITONEAL DIALYSIS APPARATUS

FIELD OF THE INVENTION

The present invention relates to a peritoneal dialysis apparatus using a disposable cassette (peritoneal dialysis circuit) integrally formed with a diaphragm and heating portion.

BACKGROUND OF THE INVENTION

The recent dialysis process employing peritoneal dialysis has been attracting attention because the cost of treatment is less expensive than with the dialysis process employing an artificial kidney and peritoneal adhesion can be prevented.

According to a peritoneal dialysis apparatus used in the dialysis process employing peritoneal dialysis, generally, a fluid infusing bag connected to a dialysis fluid container (bag) containing a peritoneal dialysis fluid (to be referred to as a dialysis fluid hereinafter) to be infused or delivered to inside the patient's peritoneum (peritoneal cavity) and a reservoir bag connected to a drained fluid container (bag) for recovering the dialysis fluid drained from the patient are placed in a pressure chamber and are used. More specifically, the pressure chamber for accommodating the fluid infusing bag and reservoir bag is formed in the dialysis apparatus body of the peritoneal dialysis apparatus. When the pressure in the pressure chamber is increased or decreased, the fluid infusing bag or reservoir bag pumps. The dialysis apparatus body has a heater for heating the dialysis fluid in the fluid infusing bag to a temperature within a predetermined temperature range.

In the conventional peritoneal dialysis apparatus, the chamber and heater must have sizes corresponding to the fluid infusing bag and reservoir bag, and the peritoneal dialysis apparatus itself becomes large in size as well as in weight. For this reason, in the site of medial treatment, particularly in home medical treatment, a large space for the peritoneal dialysis apparatus is needed in the house, and handling such as transportation of the peritoneal dialysis apparatus becomes cumbersome to interfere with a smooth medical care.

Japanese Patent No. 3113887 proposes a peritoneal dialysis apparatus in which when selecting the flow path of the disposable cassette, it can be switched by opening/closing a valve with a valve actuator. Japanese Patent Laid-Open No. 11-347115 proposes a disposable cassette integrally having a heating portion and a pump (diaphragm) for distributing a peritoneal dialysis fluid. This cassette is heated from the two sides, and the heated peritoneal dialysis fluid is distributed into the patient's peritoneal cavity with two pumps (diaphragms).

With the former apparatus, since the valve actuator is operated intermittently, the working noise of the valve is generated in the nighttime dialysis while the patient is a sleep, which offends his or her ears.

With the latter apparatus, the heating ability is not sufficient with respect to the fluid distributing ability of the pump.

The continuous ambulatory peritoneal dialysis (to be also referred to as "CAPD" hereinafter) has been attracting great attention because with which the patient himself or herself can exchange the dialysis fluid container (bag) at home or in the office, allowing him to lead normal life.

According to the CAPD, a catheter tube (peritoneal catheter) is placed in the patient's peritoneal cavity. A transfer tube is connected to the end of the catheter tube outside the body. A bag tube for a dialysis fluid bag (fluid infusing bag) containing a dialysis fluid is connected to the transfer tube. The dialysis fluid in the bag is infused into the peritoneal cavity through the respective tubes, and dialysis is performed for a predetermined period of time. After that, the spent dialysis fluid in the peritoneal cavity is recovered in a drained fluid bag through the respective tubes. Two tubes are connected to each other in an aseptic condition by fitting the male and female connectors mounted on their ends.

In the CAPD, the dialysis fluid is infused to inside the peritoneum by placing the dialysis fluid bag at a position higher than the patient's abdomen by about 1 m and transferring the dialysis fluid from the dialysis fluid bag into the abdomen inside the peritoneum under the gravity. The spent dialysis fluid from inside the peritoneum is recovered by placing the drained fluid bag at a position lower than the patient's abdomen by about 1 m and transferring the dialysis fluid from inside the peritoneum to the drained fluid bag under the gravity.

According to this dialysis fluid infusing and draining method, when peritoneal dialysis is to be performed while the patient sleeps, the patient must be laid at a position higher than the floor by about 70 cm to 100 cm by using a bed, and the dialysis fluid bag must be set at a position higher than the patient by about 1 m. As a result, the height of the entire apparatus becomes as large as about 2 m. Then, the apparatus is difficult to handle and transport. Moreover, if the patient turns over during sleeping, the apparatus might fall. Since a gravity necessary for draining the fluid must be maintained, the patient's sleeping position (height) cannot be freely selected.

In order to make up these drawbacks, a peritoneal dialysis apparatus has been proposed in which fluid infusion and draining are automated and the heights of the positions to set the dialysis fluid bag and drained fluid bag are not limited. For example, Japanese Patent No. 3113887 proposes a peritoneal dialysis apparatus in which when selecting the flow path of the disposable cassette, it can be switched by opening/closing a valve with a valve actuator. Japanese Patent Laid-Open No. 11-347115 proposes a disposable cassette integrally having a heating portion and a pump (diaphragm) for distributing a peritoneal-dialysis fluid. This cassette is heated from the two sides, and the heated peritoneal dialysis fluid is distributed into the patient's peritoneal cavity with two pumps (diaphragms).

However, in order to perform peritoneal dialysis at home by using such a peritoneal dialysis apparatus, the patient must be sufficiently trained so he can utilize the peritoneal dialysis apparatus, must memorize all the procedures by himself, and must operate the peritoneal dialysis apparatus correctly. This is no small burden to the patient.

If a minor trouble should occur in the operation procedures, he may not be able to cope with it immediately.

SUMMARY OF THE INVENTION

The present invention has been made in consideration of the above problems, and has as its object to provide a compact, lightweight peritoneal dialysis apparatus using a disposable cassette integrally formed with a diaphragm and heating portion, in which the flow path can be switched quietly and the heating ability is high.

In addition, it is another object of the present invention to provide a peritoneal dialysis apparatus in which a detachable cassette can be loaded reliably and easily by anyone while a sufficiently high heating ability is maintained.

It is still another object of the present invention to provide a peritoneal dialysis apparatus with which automatic dialysis treatment can be performed by the patient himself and the operation procedures of which are very clear and easy to understand, so dialysis treatment can be performed with optimal conditions.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 8A is a schematic view showing a state wherein a dialysis fluid is being distributed into the peritoneal cavity, and FIG. 8B is a schematic view showing a state wherein the drained fluid is being transferred;

FIG. 12 is a stereoscopic exploded view of left and right cassette locking pawl members 211 formed on an elevating member 222;

FIGS. 22, 23, 24, 25, 26, and 27 are views showing the display screen of a display 23 which sequentially changes.

The present invention has various types of arrangements defined by claims, and naturally is not limited by the arrangement of the embodiment to be described hereinafter.

DETAILED DESCRIPTION OF THE PREFERRED EMBODIMENT

Figure 1:
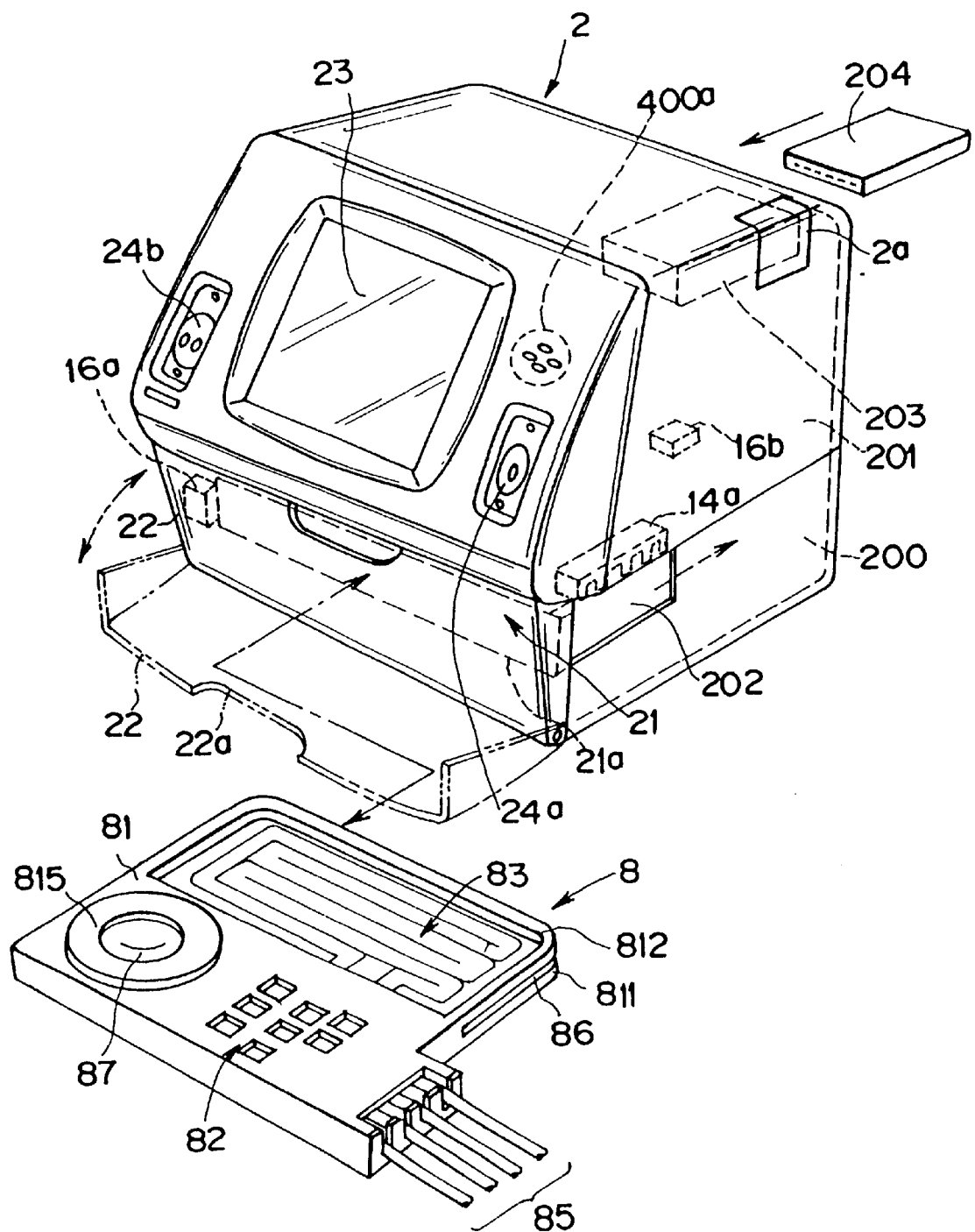
FIG. 1 is an outer appearance perspective view showing a peritoneal dialysis apparatus according to the present invention together with a cassette 8.

A peritoneal dialysis apparatus according to the present invention will be described in detail by way of a preferred embodiment shown in the accompanying drawings. FIG. 1 is an outer appearance perspective view showing the peritoneal dialysis apparatus according to the present invention together with a disposable cassette (peritoneal dialysis circuit) 8, and FIG. 2 is a schematic view showing the entire arrangement.

Figure 2:
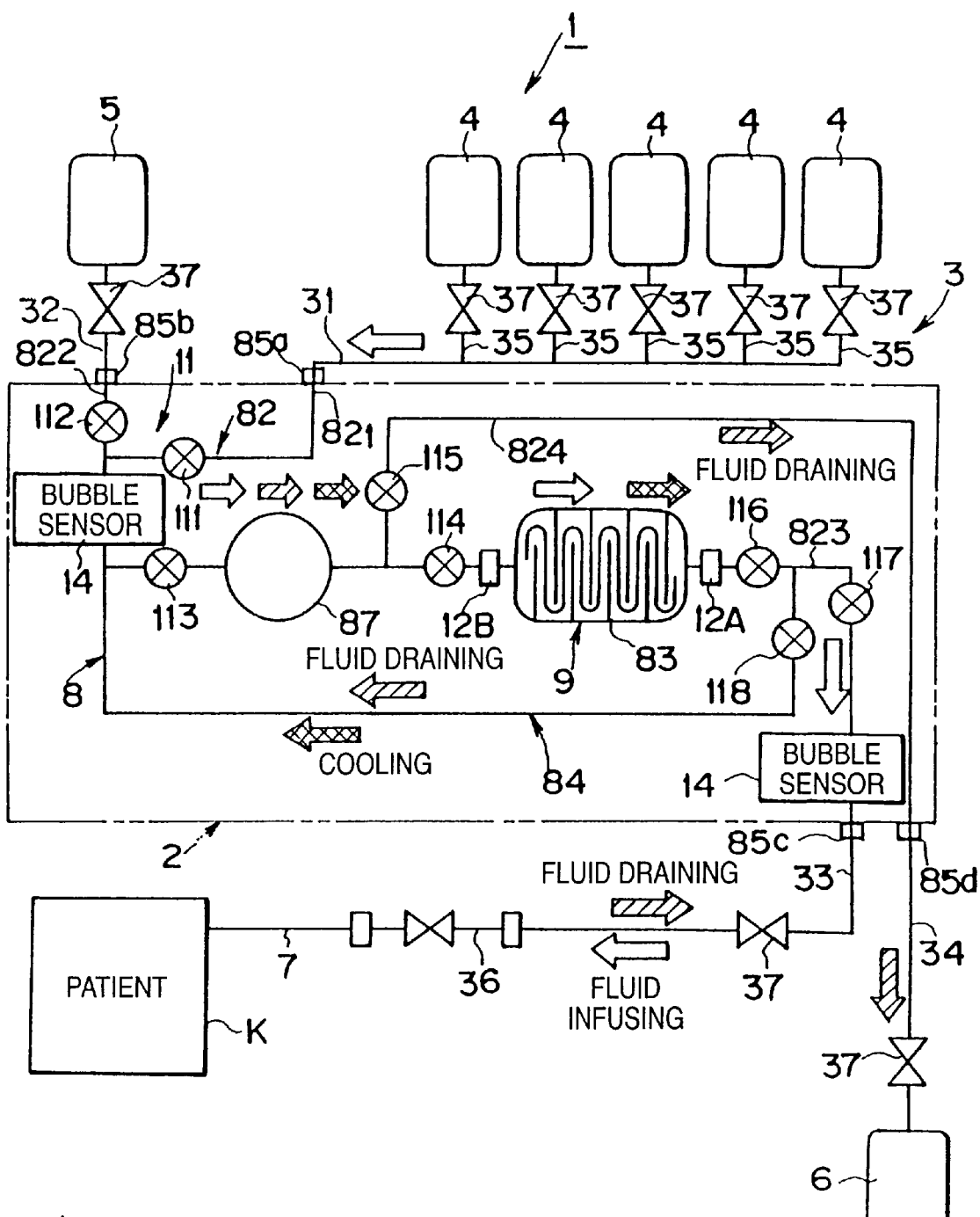
FIG. 2 is a view schematically showing a peritoneal dialysis apparatus according to an embodiment of the present invention.

Referring to FIGS. 1 and 2, a peritoneal dialysis apparatus 1 has a dialysis apparatus body 2 and a cassette 8 for the peritoneal dialysis apparatus which is detachably mounted on the dialysis apparatus body 2.

Referring to FIG. 1, the dialysis apparatus body 2 has a cassette mounting portion 21 with an opening 21a, indicated by an alternate long and two short dashed line, for mounting the cassette 8 from the front surface, a lid member 22 pivoted by holding a holding portion 22a to a position indicated by a solid line and a position indicated by a broken line so as to close and open the cassette mounting portion 21, a display 23, an operating portion (start switch) 24a for performing operation to start treatment, and an operating portion (stop switch) 24b for performing operation to stop treatment.

The operating portions 24a and 24b have shapes and colors that differ in the vertical direction so that they can be easily discriminated from each other. The operating portion 24a has one projection, while the operating portion 24b has two projections. The operating portions 24a and 24b are separate from each other with the display 23 between them in order to prevent erroneous operation.

For example, the display 23 is formed of a touch panel with a liquid crystal (LCD) panel or the like. In response to touch operation of the touch panel, the display 23 displays various types of information necessary for dialysis and indicates the user to operate the apparatus together with a voice guide, so that operability and convenience are ensured.

The dialysis apparatus body 2 has a main base 200 and sub-base 201 indicated by broken lines as the attaching base. Resin covers shown in FIG. 1 are provided to the main base 200 and sub-base 201. The main base 200 and sub-base 201 are formed of aluminum plates with a thickness of 1 mm to 2 mm, with large holes being formed at necessary portions, thus reducing the weight. Lightweight resin covers are fixed to the main base 200 and sub-base 201. For example, a memory card 204 with a memory capacity of 100 megabytes or more is provided such that it can be loaded in a card reader 203 (indicated by a broken line) from the rear surface of the apparatus. Thus, the display content of the display 23, the voice guide, and specifications for different countries can be changed quickly.

A blocking plate 202 is provided to the right surface of the cassette mounting portion 21 indicated by an alternate long and two short dashed line, to be movable in the direction of an arrow indicated by a broken line. The blocking plate 202 prevents mechanical interference with connection tubes 85 of the cassette 8, so the cassette 8 can be set at a loading position.

The cassette 8 is comprised of a cassette body 81 with such a shape that it can be mounted on and detached from the cassette mounting portion 21 of the dialysis apparatus body 2, a lower body frame 811 continuously extending from the cassette body 81, and an upper body frame 812 extending from the lower body frame 811 to oppose it through a gap 86.

The cassette body 81 integrally has a fluid transfer diaphragm 87, a heating portion 83, and a flow path switching portion, as shown in FIG. 1, and the diaphragm 87 is surrounded by a flange member 815.

Referring to FIG. 2, the peritoneal dialysis apparatus 1 has a dialysis fluid circuit unit 3. The dialysis fluid circuit unit 3 is prepared such that it is connected a plurality of dialysis fluid bags (dialysis fluid containers) 4 containing (storing) the dialysis fluid to be infused (delivered) to inside the peritoneum (peritoneal cavity) of a patient K, an additional dialysis fluid bag 5 containing a dialysis fluid with a different concentration, a drained fluid tank (drained fluid container) 6 for recovering the dialysis fluid drained from inside the peritoneum of the patient K, and a dialysis catheter (catheter tube) 7 placed inside the peritoneum of the patient K.

The dialysis fluid circuit unit 3 has a fluid infusing tube circuit 31, additional fluid infusing tube circuit 32, fluid infusing/draining tube circuit 33, and fluid draining tube circuit 34. The dialysis fluid circuit unit 3 also has a switching cassette circuit 82, heating cassette circuit 83, and bypass circuit (patient-side tube circuit) 84 provided to the cassette body 81 of the cassette 8. The switching cassette circuit 82 is comprised of a fluid infusing circuit 821, additional fluid infusing circuit 822, fluid infusing/draining circuit 823, and fluid draining circuit 824.

Figure 3:
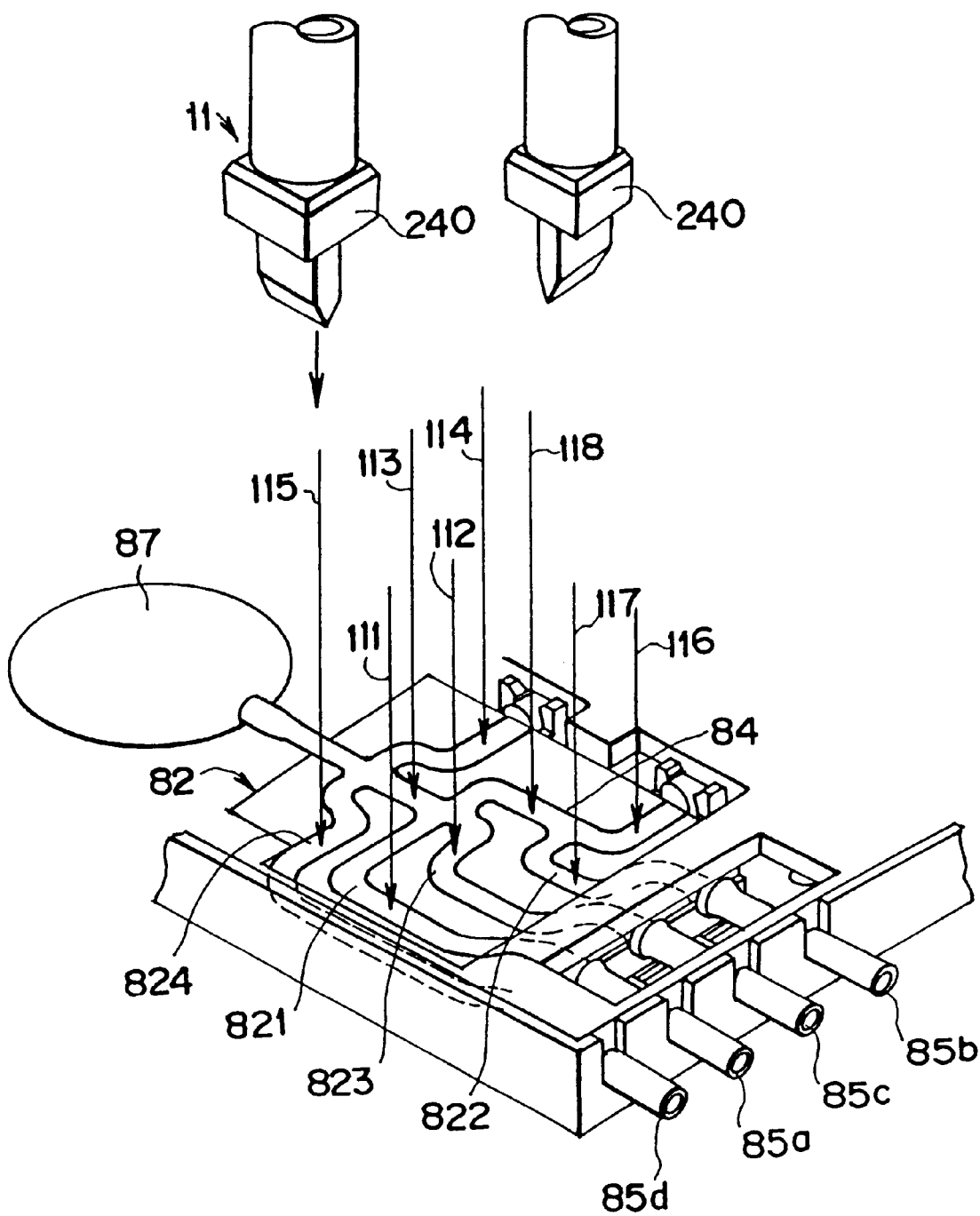
FIG. 3 is an outer appearance perspective view showing a flow path switching portion for the cassette 8 and clampers 240.

In the outer appearance perspective view of FIG. 3 showing the flow path switching portion for the cassette 8 and clampers (clamps) 240, one end of the fluid infusing circuit 821, one end of the additional fluid infusing circuit 822, the other end of the fluid infusing/draining circuit 823, and the other end of the fluid draining circuit 824 are connected to connection tubes 85a, 85b, 85c, and 85d, respectively.

In FIG. 2, one end side of the fluid infusing tube circuit 31 is branch-connected to a plurality of branch tube circuits 35. One end of each branch tube circuit 35 is connected to the corresponding dialysis fluid bag 4, and the other end of the fluid infusing tube circuit 31 is connected to one end of the fluid infusing circuit 821 through the connection tube 85a.

One end of the additional fluid infusing tube circuit 32 is connected to the additional dialysis fluid bag 5, and the other end thereof is connected to one end of the additional fluid infusing circuit 822 through the connection tube 85b.

One end of the fluid infusing/draining tube circuit 33 is connected to the other end of the fluid infusing/draining circuit 823 through the connection tube 85c, and the other end thereof is connected to the dialysis catheter 7 through a transfer tube set 36. One end of the fluid draining tube circuit 34 is connected to the other end of the fluid draining circuit 824 through the connection tube 85d, and the other end thereof is connected to the drained fluid tank 6.

When the cassette 8 is mounted in the dialysis apparatus body 2, the fluid infusing tube circuit 31, additional fluid infusing tube circuit 32, fluid infusing/draining tube circuit 33, and fluid draining tube circuit 34 connected to the switching cassette circuit 82 are located on the front surface or near-front side surface of the dialysis apparatus body 2.

Each of the branch tube circuits 35, additional fluid infusing tube circuit 32, fluid infusing/draining tube circuit 33, and fluid draining tube circuit 34 has a forceps (flow path opening/closing means) 37 for opening/closing the corresponding flow path.

Figure 4:
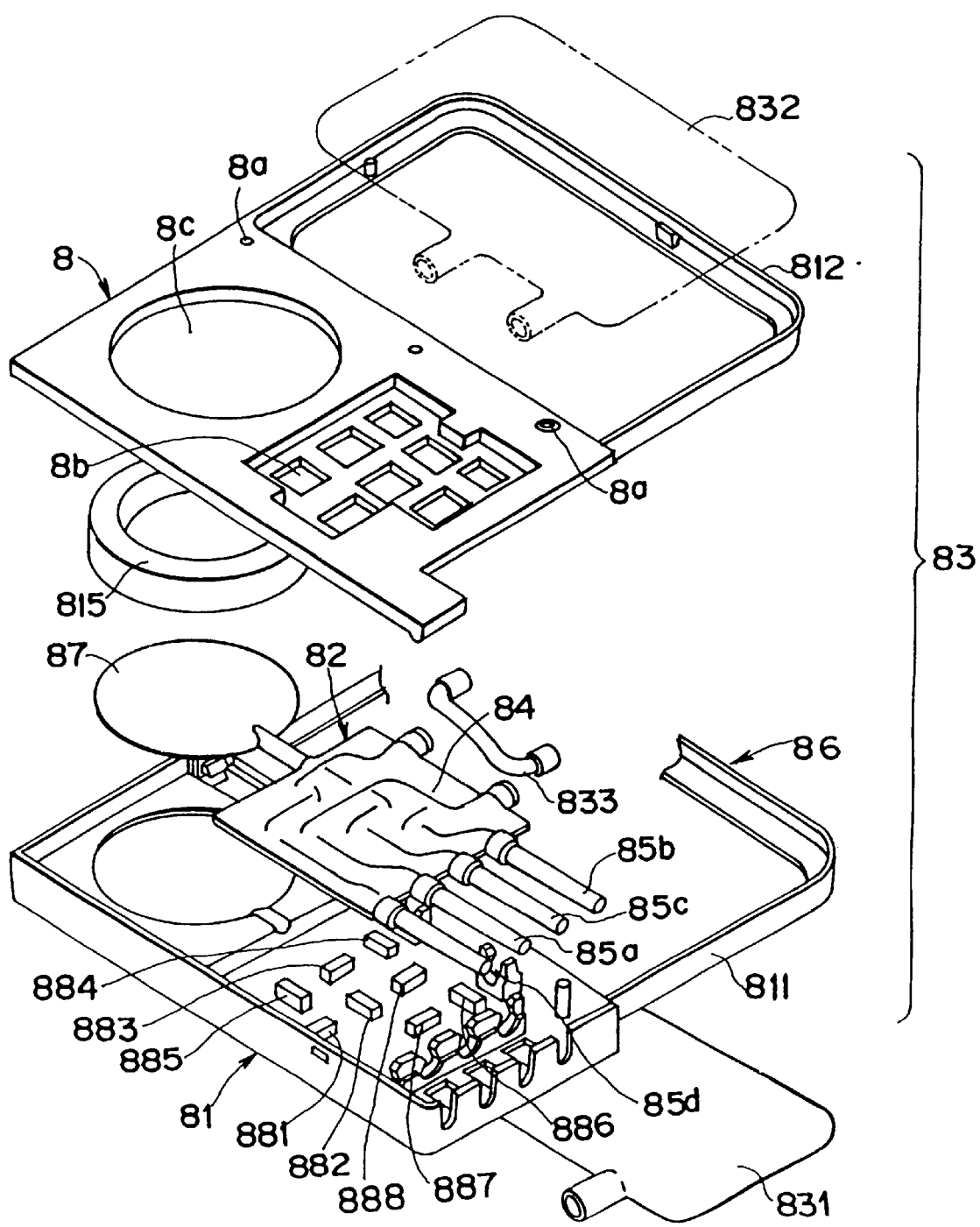
FIG. 4 is a stereoscopic exploded view of the cassette 8.

FIG. 4 is a stereoscopic exploded view of the cassette 8. In FIG. 4, constituent components that have already been described are denoted by the same reference numerals, and a detailed description thereof will be omitted. The gap 86 is formed between two divisional cassette heating circuits 831 and 832. When the cassette body 81 is mounted in the cassette mounting portion 21 of the dialysis apparatus body 2, the heaters (heating portions) of a heating means 9 are located to face the two surfaces (upper and lower surfaces) of the divisional cassette heating circuits 831 and 832, so that the divisional cassette heating circuits 831 and 832 are heated as they are sandwiched by the corresponding heaters.

The cassette body 81 has the switching cassette circuit 82 shown in FIG. 1. The switching cassette circuit 82 is comprised of the fluid infusing circuit 821, additional fluid infusing circuit 822, fluid infusing/draining circuit 823, and fluid draining circuit 824 shown in FIG. 3. The other end of the additional fluid infusing circuit 822 communicates with midway along the fluid infusing circuit 821, and one end of the fluid draining circuit 824 communicates with near the other end of the fluid infusing circuit 821.

When the cassette body 81 is mounted in the cassette mounting portion 21 of the dialysis apparatus body 2, the switching cassette circuit 82 can be switched between the fluid infusing circuit state and fluid draining circuit state by the closing operation of the clampers 240 shown in FIG. 3.

The fluid infusing circuit state is a state wherein the fluid infusing circuit 821 (or additional fluid infusing circuit 822) and fluid infusing/draining circuit 823 communicate with each other, so that the dialysis fluid bags 4 (or additional dialysis fluid bag 5) and dialysis catheter 7 communicate with each other, in other words, a state necessary for infusing the dialysis fluid to inside the peritoneum of the patient K (a state wherein the dialysis fluid can be infused).

The fluid draining circuit state is a state wherein the fluid infusing/draining circuit 823 and fluid draining circuit 824 communicate with each other, so that the dialysis catheter 7 and drained fluid tank 6 communicate with each other, in other words, a state necessary for draining the dialysis fluid from inside the peritoneum of the patient K (a state wherein the dialysis fluid can be drained). The cassette body 81 also has the heating cassette circuit 83 shown in FIG. 4. The heating cassette circuit 83 has two sheet-like divisional cassette heating circuits 831 and 832 opposing each other.

One end of the lower divisional cassette heating circuit 831 communicates with the other end of the fluid infusing circuit 821, and the other end thereof communicates with one end of the upper divisional cassette heating circuit 832 through a connection pipe 833. The other end of the upper divisional cassette heating circuit 832 communicates with one end of the fluid infusing/draining circuit 823.

Accordingly, the dialysis fluid sequentially flows through the lower and upper divisional cassette heating circuits 831 and 832 in this order.

In the present invention, the dialysis fluid may be divided to flow through the lower and upper divisional cassette heating circuits 831 and 832, and the divided flows may thereafter merge.

Figure 5:
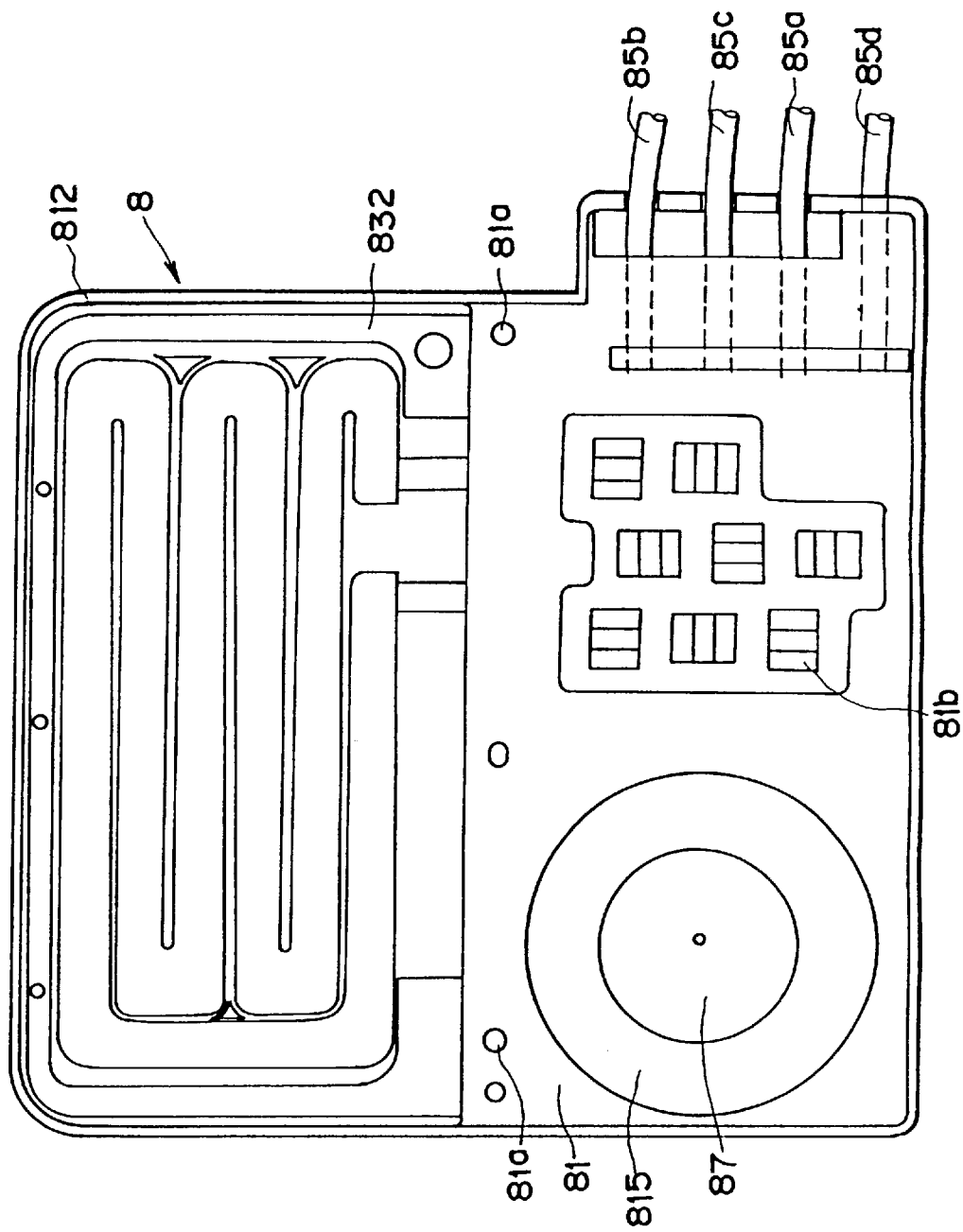
FIG. 5 is a plan view of the cassette 8.
Figure 6:
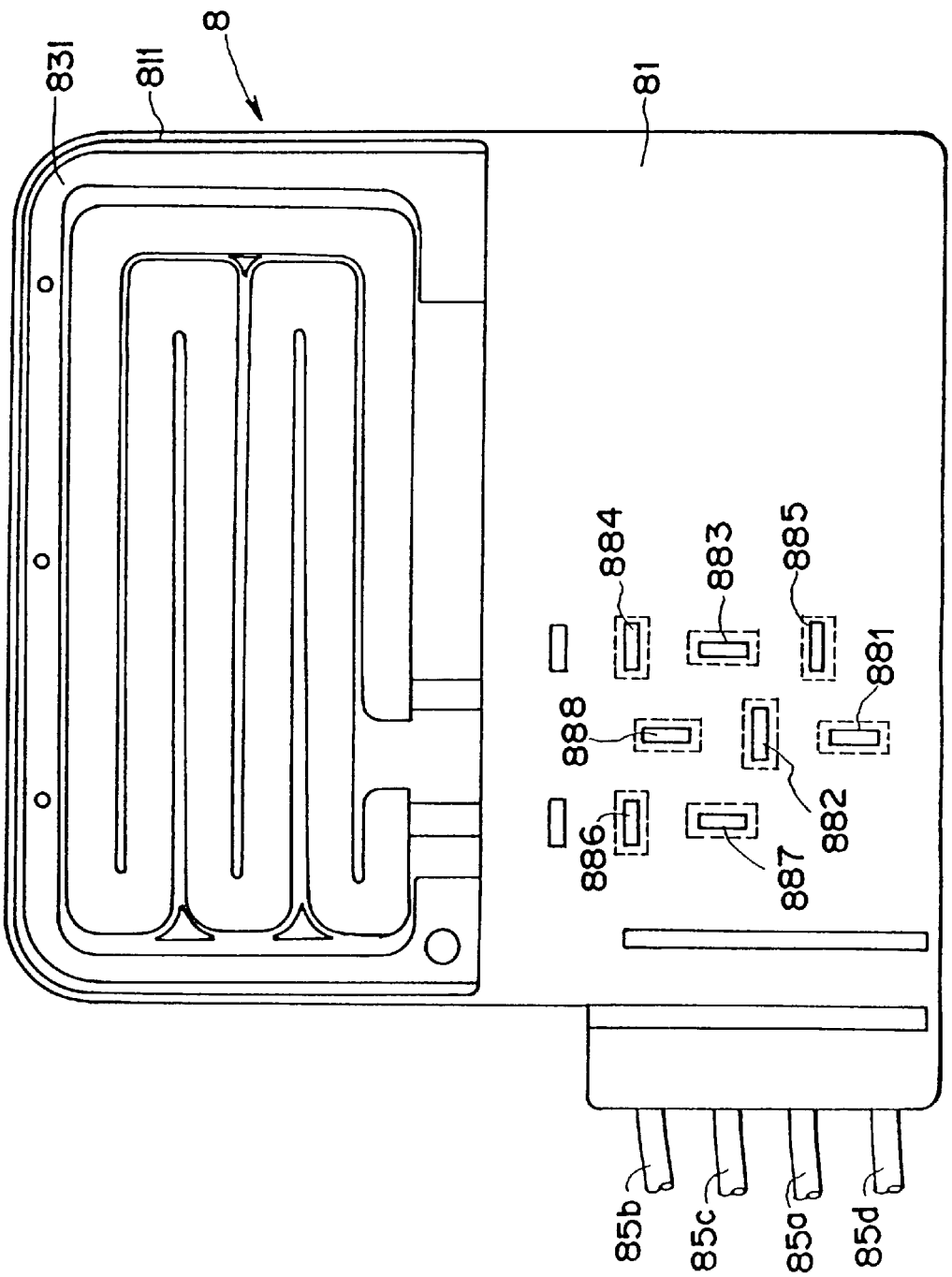
FIG. 6 is a rear view of the cassette 8.

The flow paths of the divisional cassette heating circuits 831 and 832 meander as shown in the plan view of the cassette 8 of FIG. 5 and the rear view of the cassette 8 of FIG. 6. Alternatively, the flow paths of the divisional cassette heating circuits 831 and 832 may swirl. When they meander or swirl in this manner, the flow paths of the divisional cassette heating circuits 831 and 832 become long, so that the dialysis fluid can be heated reliably.

The cassette body 81 is provided with a diaphragm pump 87 which is held in an airtight state in a pump chamber (to be described later) in order that it pumps through contraction and expansion to distribute the dialysis fluid. The diaphragm pump 87 is connected to midway along the fluid infusing circuit 821.

The diaphragm pump 87 is accommodated in an airtight manner with the flange member 815. When the pressure is increased, the diaphragm pump 87 contracts. When the pressure is reduced, the diaphragm pump 87 expands.

The cassette body 81 has the bypass circuit 84, as described above. One end of the bypass circuit 84 is connected to the upstream of the heating cassette circuit 83, i.e., midway along the fluid infusing circuit 821 in this embodiment, and the other end thereof is connected to the downstream of the heating cassette circuit 83, i.e., midway along the fluid infusing/draining circuit 823 in this embodiment. The bypass circuit 84 connects the upstream and downstream of the heating cassette circuit 83, thus forming a circulatory circuit for cooling the dialysis fluid.

The bypass circuit 84 may have a compulsory cooling means such as a Peltier element for compulsorily cooling the dialysis fluid, so the dialysis fluid is cooled quickly and reliably.

The switching cassette circuit 82, heating cassette circuit 83, bypass circuit 84, and diaphragm pump 87 are arranged substantially in a planar manner. This can further reduce the thickness of the cassette 8.

When the cassette body 81 is mounted in the cassette mounting portion 21 of the dialysis apparatus body 2, the outlet side (downstream) of the heating cassette circuit 83 can be switched between a final fluid infusing circuit state and a return circuit state. The final fluid infusing circuit state is a state wherein the outlet side of the heating cassette circuit 83 communicates with the fluid infusing/draining circuit 823 and does not communicate with the bypass circuit 84. The return circuit state is a state wherein the outlet side of the heating cassette circuit 83 communicates with the bypass circuit 84 and does not communicate with the fluid infusing/draining circuit 823.

As shown in FIGS. 4 and 6, first to eighth support projections 881 to 888 forming the flow path switching portion are formed at that portion of the lower body frame 811 which corresponds to the switching cassette circuit 82. The first support projection 881 supports a portion near one end of the fluid infusing circuit 821, the second support projection 882 supports the additional fluid infusing circuit 822, the third support projection 883 supports that portion of the fluid infusing circuit 821 which is between the diaphragm pump 87 and one end of the bypass circuit 84, and the fourth support projection 884 supports that portion of the fluid infusing circuit 821 which is between the diaphragm pump 87 and one end of the heating cassette circuit 83. Similarly, the fifth support projection 885 supports the fluid draining circuit 824, the sixth support projection 886 supports that portion of the fluid infusing/draining circuit 823 which is between the other end of the heating cassette circuit 83 and the other end of the bypass circuit 84, the seventh support projection 887 supports a portion near the other end of the fluid infusing/draining circuit 823, and the eighth support projection 888 supports the bypass circuit 84.

The switching cassette circuit 82, bypass circuit 84, and diaphragm pump 87 are integrally formed by blow molding. This can reduce bonding using separate components, so that the quality of the cassette 8 is improved and the cost can be reduced.

The divisional cassette heating circuits 831 and 832 of the heating cassette circuit 83 are formed by sheet molding. This can simplify manufacture of the divisional cassette heating circuits 831 and 832 and can reduce the cost.

The switching cassette circuit 82, bypass circuit 84, and diaphragm pump 87 are bonded to the divisional cassette heating circuits 831 and 832 by RF fusion (RF welding) or adhesion.

To form the divisional cassette heating circuits 831 and 832 by sheet molding, for example, two resin sheets are overlaid, and are fused with a predetermined pattern. Portions that are not fused form flow paths.

As the material to form the switching cassette circuit 82, heating cassette circuit 83, bypass circuit 84, and diaphragm pump 87, a soft resin, e.g., polyolefin such as polyethylene, polypropylene, an ethylene-propylene copolymer, or an ethylene-vinyl acetate copolymer (EVA), polyester such as polyvinyl chloride, polyvinylidene chloride, polystyrene, polyamide, polyimide, poly-(4-methylpentene-1), ionomer, acrylic resin, polyethylene terephthalate (PET), or polybutylene terephthalate (PBT), various types of thermoplastic elastomers such as styrene-, polyolefin-, polyvinyl chloride-, polyurethane-, polyester-, or polyamide-based elastomer, silicone resin, or polyurethane; or a copolymer, blend, or polymer alloy mainly containing any one of these substances. One or more of the members cited above may be combined (as a laminate of 2 layers or more) and used to form the above components.

Referring to FIG. 5, the cassette body 81 has positioning holes 81a to enable positioning with positioning pins (to be described later) Openings 81b that form part of the flow path switching portion are formed to oppose the first to eighth support projections. The clampers enter the openings 81b to close them.

Figure 7:
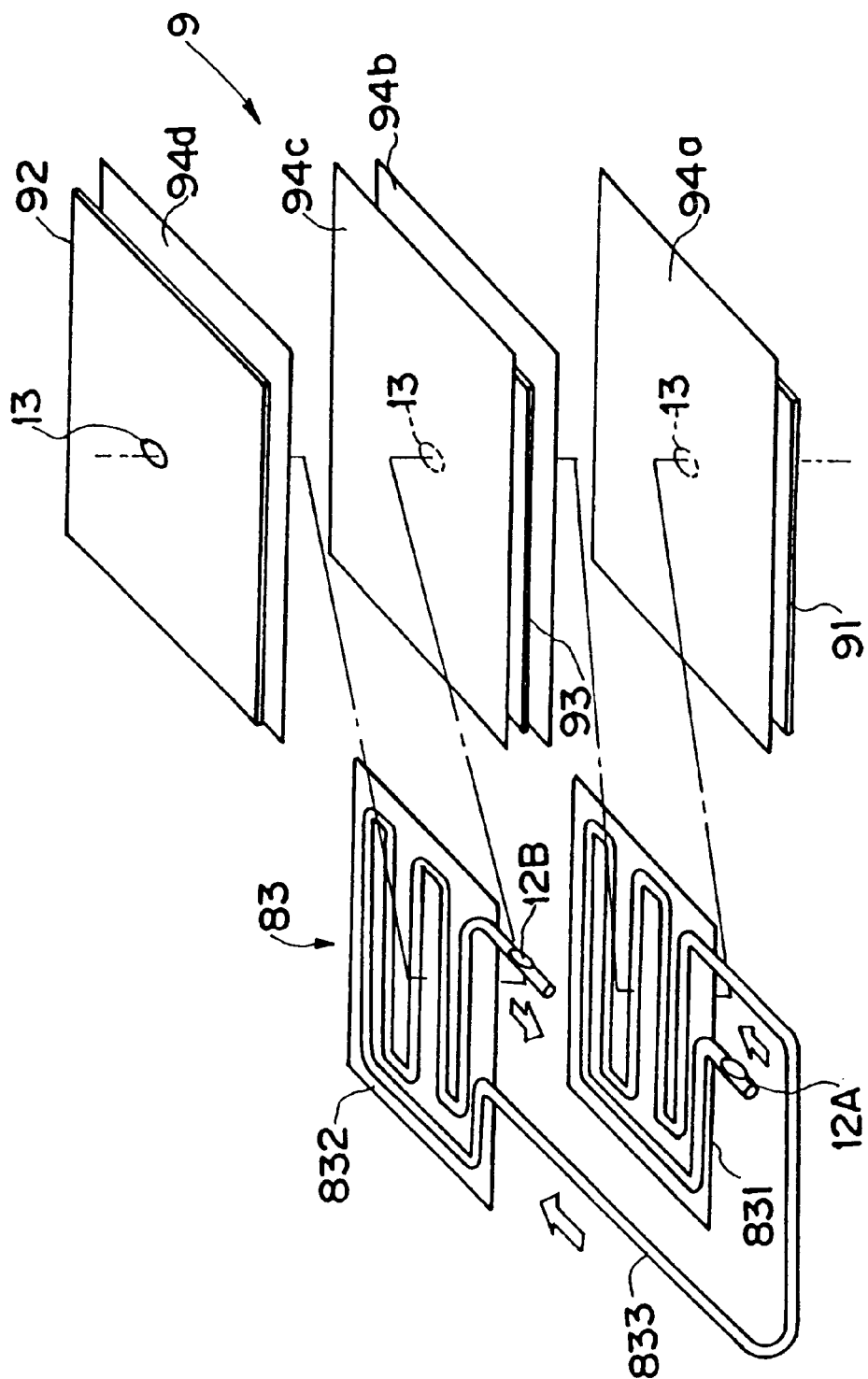
FIG. 7 is a view showing the relationship between the heating circuit for the cassette 8 and a heater.

As shown in FIG. 7 indicating the heater arrangement, the heating means 9 for heating the heating cassette circuit 83 of the cassette 8 is formed in the dialysis apparatus body 2. The heating means 9 has a plate-like (layer-like) lower sheet heater 91, plate-like (layer-like) upper sheet heater 92, and plate-like (layer-like) intermediate sheet heater 93.

The lower sheet heater 91 heats the lower surface of the lower divisional cassette heating circuit 831 from below through an aluminum plate 94a serving as a heat transfer member, and the upper sheet heater 92 heats the upper surface of the upper divisional cassette heating circuit 832 from above through an aluminum plate 94d serving as a heat transfer member. The intermediate sheet heater 93 is located in the gap 86, and heats the upper surface of the lower divisional cassette heating circuit 831 from above through an aluminum plate 94b serving as a heat transfer member and the lower surface of the upper divisional cassette heating circuit 832 from below through an aluminum plate 94c serving as a heat transfer member.

Thus, the dialysis fluid in the lower divisional cassette heating circuit 831 is heated as it is sandwiched between the lower and intermediate sheet heaters 91 and 93, and the dialysis fluid in the upper divisional cassette heating circuit 832 is heated as it is sandwiched between the upper and intermediate sheet heaters 92 and 93. Therefore, the heating efficiency of the heating means 9 for the dialysis fluid in the heating cassette circuit 83 is improved, which is advantageous for downsizing and weight reduction of the dialysis apparatus body 2 and cassette 8.

A clamp means 11 shown in FIG. 3 switches the switching cassette circuit 82 of the cassette 8 to one of the fluid infusing circuit state and fluid draining circuit state, switches the outlet side of the heating cassette circuit 83 to one of the final fluid infusing circuit state and fluid draining circuit state, and aids pumping of the diaphragm pump 87.

More specifically, first to eighth clamps 111 to 118 indicated by arrows are formed in the dialysis apparatus body 2.

The first clamp 111 cooperates with the first support projection 881 to clamp a portion near one end of the fluid infusing circuit 821 so that the flow path is closed. The second clamp 112 cooperates with the second support projection 882 to clamp the additional fluid infusing circuit 822 so that the flow path is closed. The third clamp 113 cooperates with the third support projection 883 to clamp that portion of the fluid infusing circuit 821 which is between the diaphragm pump 87 and one end of the bypass circuit 84, so that the flow path is closed. The fourth clamp (pumping control clamp) 114 cooperates with the fourth support projection 884 to clamp that portion of the fluid infusing circuit 821 which is between the diaphragm pump 87 and one end of the heating cassette circuit 83, so that the flow path is closed.

Similarly, the fifth clamp 115 cooperates with the fifth support projection 885 to clamp the fluid draining circuit 824 so that the flow path is closed. The sixth clamp 116 cooperates with the sixth support projection 886 to clamp that portion of the fluid infusing/draining circuit 823 which is between the other end of the heating cassette circuit 83 and the other end of the bypass circuit 84, so that the flow path is closed. The seventh clamp 117 cooperates with the seventh support projection 887 to clamp a portion near the other end of the fluid infusing/draining circuit 823, so that the flow path is closed. The eighth clamp 118 cooperates with the eighth support projection 888 to clamp the bypass circuit 84 so that the flow path is closed. Hence, when switching the switching cassette circuit 82 to the fluid infusing circuit state, the first clamp 111 (or second clamp 112), fourth clamp (pumping control clamp) 114, and sixth and seventh clamps 116 and 117 are switched to the unclamp state, and the second clamp 112 (or first clamp 111) and fifth and eighth clamps 115 and 118 are switched to the clamp state. When pressurizing the interior of a chamber 814 with a pumping actuating means 10, the fourth clamp 114 is switched to the unclamp state, and the third clamp 113 is switched to the clamp state. When reducing the pressure in the chamber 814 with the pumping actuating means 10, the fourth clamp 114 is switched to the clamp state, and the third clamp 113 is switched to the unclamp state. As a result, the dialysis fluid can be distributed, i.e., infused, from the dialysis fluid bags 4 (or additional dialysis fluid bag 5) toward the dialysis catheter 7, thus achieving a state shown in FIG. 8A wherein the dialysis fluid can be distributed into the peritoneal cavity.

When switching the switching cassette circuit 82 to the fluid draining circuit state, the seventh and eighth clamps 117 and 118 are switched to the unclamp state, and the first, second, fourth, and sixth clamps 111, 112, 114, and 116 are switched to the clamp state, thus achieving the state shown in FIG. 8B wherein the drained fluid can be recovered.

When reducing the pressure in the pump chamber with the pumping actuating means 10, the third clamp 113 is switched to the unclamped state, and the fifth clamp 115 is switched to the clamp state. When pressurizing the interior of the chamber 814 with the pumping actuating means 10, the third clamp 113 is switched to the clamp state, and the fifth clamp 115 is switched to the unclamp state, so that the dialysis fluid can be drained from the dialysis catheter 7 toward the drained fluid tank 6.

The diaphragm pump 87, third to fifth clamps 113 to 115, and pumping actuating means 10 make up a fluid distributing (infusing) means for distributing the dialysis fluid.

When the switching cassette circuit 82 is in the fluid infusing circuit state and the outlet side of the heating cassette circuit 83 is in the final fluid infusing circuit state, the seventh clamp 117 is in the unclamp state, while the eighth clamp 118 is in the clamp state.

When switching the outlet side of the heating cassette circuit 83 to the return circuit state, the first, second, and seventh clamps 111, 112, and 117 are switched to the clamp state, and the eighth clamp 118 is switched to the unclamp state. Thus, the dialysis fluid does not flow from the outlet side of the heating cassette circuit 83 toward the dialysis catheter 7, but flows through the bypass circuit 84 toward the diaphragm pump 87. In other words, the dialysis fluid circulates between the bypass circuit 84 and heating cassette circuit 83.

The seventh and eighth clamps 117 and 118 make up a fluid infusing/draining circuit switching means that switches the outlet side of the heating cassette circuit 83 between the final fluid infusing circuit state and the return circuit state.

When draining the dialysis fluid, the drained fluid is recovered in the drained fluid tank 6 through the bypass circuit 84. This simplifies the arrangement of the flow path.

As described above, when the cassette body 81 is provided with the switching cassette circuit 82, heating cassette circuit 83, bypass circuit 84, and diaphragm pump 87, the peritoneal dialysis apparatus 1 can be downsized and reduced in weight. Thus, handling such as transportation of the peritoneal dialysis apparatus 1 is facilitated, and a smooth medical care can be performed.

In particular, since the dialysis fluid flowing through the divisional cassette heating circuits 831 and 832 is heated as it is sandwiched by the corresponding heaters, the heating efficiency of the dialysis fluid is improved, so the peritoneal dialysis apparatus 1 can be further downsized and reduced in weight.

As shown in FIG. 2, the peritoneal dialysis apparatus 1 has various types of sensors for temperature management and the like of the dialysis fluid.

More specifically, in the dialysis apparatus body 2, a temperature sensor 12A for measuring (detecting) the temperature (outlet fluid temperature) of the dialysis fluid flowing through the outlet side (downstream) of the heating cassette circuit 83 is set downstream of the heating cassette circuit 83, and a temperature sensor 12B for measuring (detecting) the temperature (inlet fluid temperature) of the dialysis fluid flowing through the inlet side (upstream) of the heating cassette circuit 83 is set upstream of the heating cassette circuit 83.

As the temperature sensors 12A and 12B, thermopile infrared sensors (non-contact temperature sensors) with very quick response speeds are preferably used. Then, the temperatures of the sheet heaters 91, 92, and 93 can be controlled at high precision.

As shown in FIG. 7, the sheet heaters 91, 92, and 93 respectively have heater temperature sensors 13, e.g., thermisters, for measuring (detecting) their temperatures. Furthermore, the dialysis apparatus body 2 has bubble sensors 14 for detecting bubbles on the inlet and outlet sides of the switching cassette circuit 82. The peritoneal dialysis apparatus 1 has a closure sensor for detecting closure of a circuit, and various types of other sensors (various types of sensors 16).

Figure 9:
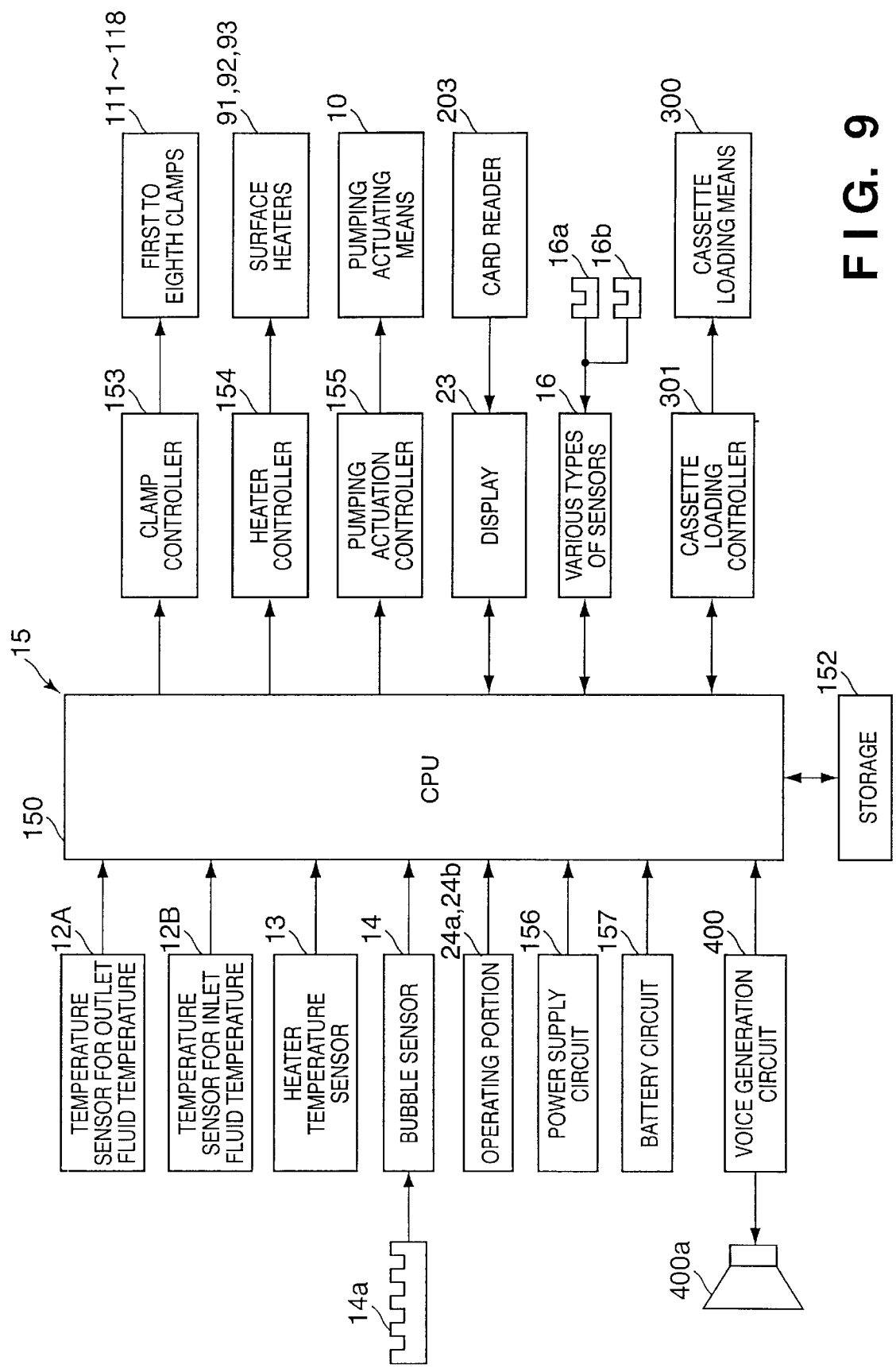
FIG. 9 is a block diagram of a dialysis apparatus body.

As shown in the block diagram of FIG. 9, the peritoneal dialysis apparatus 1 has a control system (control means) 15 for controlling infusing, draining, and the like of the dialysis fluid.

More specifically, the control system 15 has a CPU 151 and storage 152. The CPU 151 is electrically connected to a clamp controller 153 for controlling the plurality of clamps 111 to 118, a heater controller 154 for controlling the temperatures of the plurality of sheet heaters 91, 92, and 93, and a pumping actuation controller 155 for controlling the pumping actuating means 10. The CPU 151 is also electrically connected to the temperature sensor 12A for measuring the outlet fluid temperature, the temperature sensor 12B for measuring the inlet fluid temperature, the heater temperature sensors 13 for the respective heaters, the respective bubble sensors 14, the display 23, and the operating portions 24a and 24b. The CPU 151 is also electrically connected to a power supply circuit 156, a battery circuit 157, a voice generation circuit 400, and a cassette loading controller 301 for controlling a cassette loading means 300. The display 23 is electrically connected to the card reader 203 in which the memory card (described above) can be loaded.

With this control system 15, when the temperature measured by the temperature sensor 12A reaches or exceeds a preset predetermined value (39° C. in this embodiment), the clamp controller 153 controls the seventh and eighth clamps 117 and 118 to set them to the clamp state and unclamped state, respectively, and the heater controller 154 switches the plurality of sheet heaters 91, 92, and 93 to the OFF state to stop their driving operations.

Outputs (output values) from the respective sheet heaters 91, 92, and 93 are selected on the basis of the temperature control flow of the dialysis fluid and the temperature of the dialysis fluid. More specifically, the control system 15 controls the outputs (driving operations) of the plurality of sheet heaters 91, 92, and 93 on the basis of the temperatures measured by the temperature sensors 12A and 12B, so that the temperature of the dialysis fluid to be infused falls within a predetermined temperature range. The clamp controller 153 controls the first clamp 111 (or second clamp 112) and the fourth, sixth, and seventh clamps 114, 116, and 117 to switch them to the unclamp state, and controls the second clamp 112 (or first clamp 111) and the fifth and eighth clamps 115 and 118 to switch them to the clamp state. Thus, the switching cassette circuit 82 can be switched to the fluid infusing circuit state. The heater controller 154 performs control operation to supply power (output) to the plurality of sheet heaters 91, 92, and 93. Thus, the heating step of heating the dialysis fluid flowing through the heating cassette circuit 83, in other words, the dialysis fluid temperature control flow, enters the preheat step.

When a time T1 elapses since power supply to the plurality of sheet heaters 91, 92, and 93 is started, the preheat step is ended. When the preheat step is ended, the pumping actuation controller 155 controls the pumping actuating means 10 to alternately repeat pressurization and pressure reduction of the interior of the pump chamber. The clamp controller 153 controls the fourth clamp 114 to alternately repeatedly switch it to the clamp state and unclamp state in accordance with pressurization and pressure reduction in the chamber 814, and controls the third clamp 113 to alternately repeatedly switch it to the clamp state and unclamp state in accordance with pressurization and pressure reduction in the chamber 814. Thus, the diaphragm pump 87 is caused to pump (contract and expand), so the dialysis fluid is distributed from the dialysis fluid bags 4 toward the dialysis catheter 7 and infused.

When the preheat step is ended, the dialysis fluid temperature control flow enters the initial heating step. When the initial heating step is ended, the dialysis fluid temperature control flow enters the normal heating step. In the normal heating step, output control for the plurality of sheet heaters 91, 92 and 93 is performed such that, when the temperature measured by the temperature sensor 12A is less than 33° C., a heater output value obtained by P control is output to the plurality of sheet heaters 91, 92, and 93.

When the temperature measured by the temperature sensor 12A is 33° C. or more and less than 39° C., a heater output value obtained by PI control is output to the plurality of sheet heaters 91, 92, and 93.

Therefore, output control of the plurality of sheet heaters 91, 92, and 93 can be performed at high precision. In the initial heating step or normal heating step, when the temperature measured by the temperature sensor 12A becomes 39° C. or more, the clamp controller 153 controls the seventh and eighth clamps 117 and 118 to switch them to the clamp state and unclamped state, respectively. Also, the heater controller 154 stops power supply to the plurality of sheet heaters 91, 92, and 93, in other words, turns off the plurality of sheet heaters 91, 92, and 93. Therefore, the outlet side of the heating cassette circuit 83 can be switched to the return circuit state, and the dialysis fluid flows from the heating cassette circuit 83 not toward the dialysis catheter 7 but toward the bypass circuit 84, returns to the upstream of the heating cassette circuit 83 through the bypass circuit 84, and circulates between the bypass circuit 84 and heating cassette circuit 83. During this circulation, the temperature of the dialysis fluid decreases (is cooled). Namely, the dialysis fluid heating control flow advances to the cooling step (step 12). As a result, a dialysis fluid with a temperature (a temperature of 39° C. or more) considerably higher than the temperature of the patient K is not distilled to the patient K, and safe dialysis treatment can be performed.

When the temperature measured by the temperature sensor 12A becomes less than 39° C., the clamp controller 153 controls the seventh and eighth clamps 117 and 118 to switch them to the unclamp state and clamped state, respectively. Also, the plurality of sheet heaters 91, 92, and 93 are turned on. Thus, the outlet side of the heating cassette circuit 83 can be restored to the final fluid infusing circuit state, and the flow advances to the initial heating step or normal heating step again. When a predetermined amount of dialysis fluid is infused (injected) to inside the peritoneum of the patient K, infusing of the dialysis fluid is ended.

After infusing of the dialysis fluid is ended, the clamp controller 153 controls the seventh and eighth clamps 117 and 118 to switch them to the unclamp state, and controls the fourth and sixth clamps 114 and 116 to switch them to the clamp state. Thus, the switching cassette circuit 82 can be switched to the fluid draining circuit state.

The pumping actuation controller 155 controls the pumping actuating means 10 to alternately repeat pressure reduction and pressurization of the chamber 814. Also, the clamp controller 153 controls the third clamp 113 to alternately repeat switching between the unclamp state and clamp state in accordance with pressure reduction and pressurization of the interior of the chamber 814, and controls the fifth clamp 115 to alternately repeat switching between the clamp state and unclamp state in accordance with pressure reduction and pressurization of the interior of the chamber 814. Hence, the diaphragm pump 87 is caused to pump, and the dialysis fluid inside the peritoneum can be sent from the dialysis catheter 7 toward the drained fluid tank 6 and can be drained.

Figure 10:
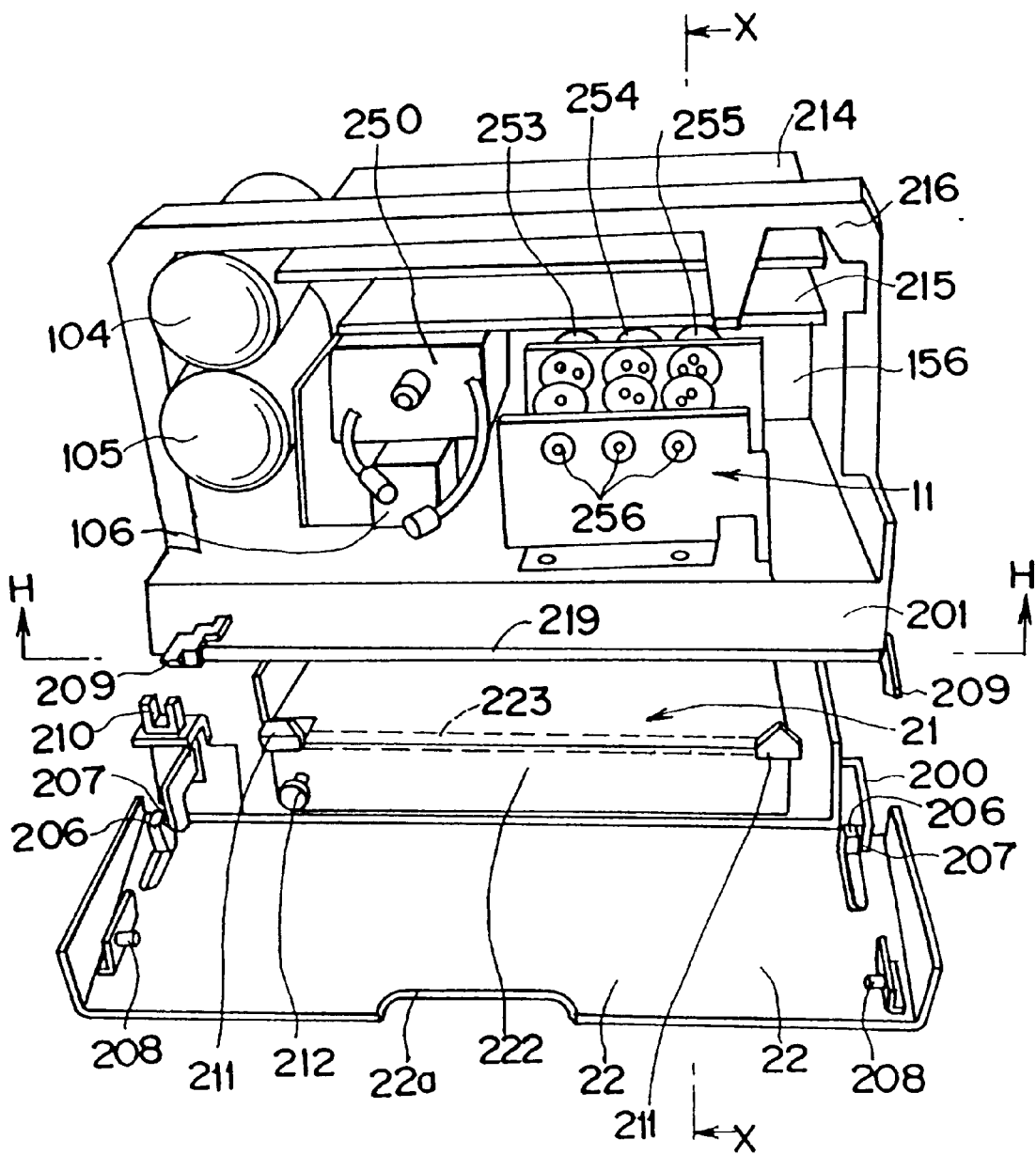
FIG. 10 is an outer appearance perspective view showing the dialysis apparatus body from which the cover is removed.

FIG. 10 is an outer appearance perspective view of the dialysis apparatus body 2 from which all the covers except the lid member 22 are removed. In FIG. 10, the lid member 22 is opened, so the opening of the cassette mounting portion 21 can be seen.

Referring to FIG. 10, constituent components that have already been described are denoted by the same reference numerals, and a detailed description thereof will be omitted. The main base 200 and sub-base 201 are formed such that they can be vertically attached to and detached from each other from a separation surface H indicated by an alternate long and short dashed line. When the main base 200 and sub-base 201 are integrally fixed by using a plurality of screws (not shown), as shown in FIG. 10, the cassette mounting portion 21 is formed. When the screws are removed, the main base 200 and sub-base 201 can be vertically separated apart from each other easily.

Left and right axial support members 206, having holes and pivotally axially supported by left and right locking members 209 fixed to a supported shaft 219 pivotally axially supported by the main base 200, are fixed to the lid member 22, and the lid member 22 is opened to the front side as shown in FIG. 10. Also, the left and right locking members 209, pivotally formed on the sub-base 201 so as to be pivoted by the shaft 219 simultaneously, lock with left and right pins 208, so the lid member 22 is maintained at the closed position. The closed state of the lid member 22 is detected by a door sensor 210 fixed to the main base 200, so the lid member 22 does not operate when it is in the open state shown in FIG. 10.

Figure 11A:
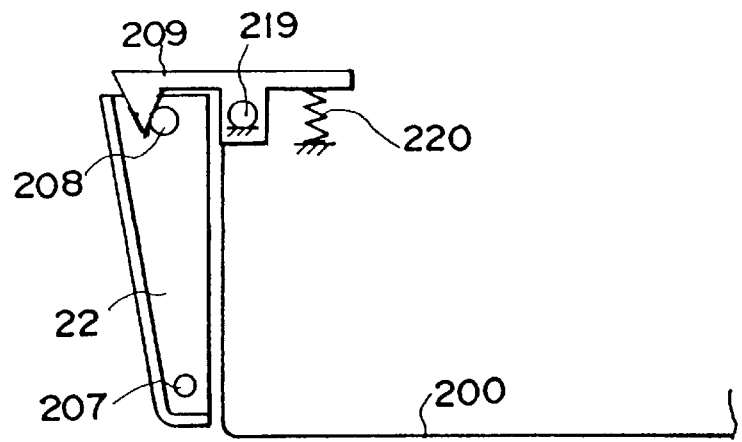
FIGS. 11A, 11B, and 11C are views for explaining the operation of a lid member 22 and correspond to a sectional view taken along the line of arrows X—X of FIG. 10.
Figure 11B:
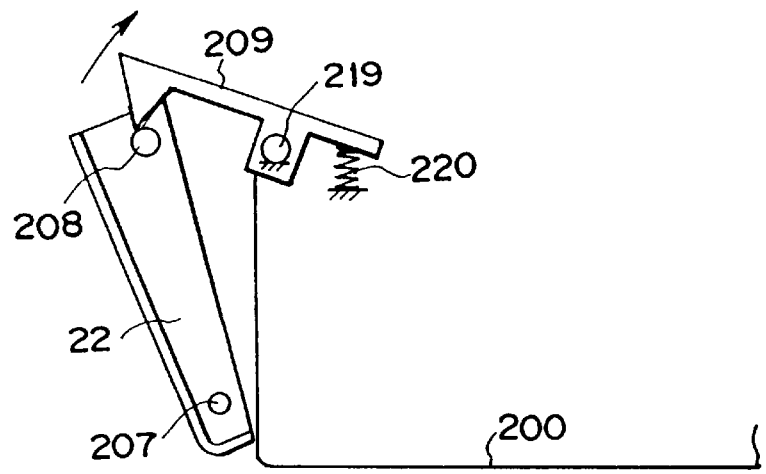
Figure 11C:
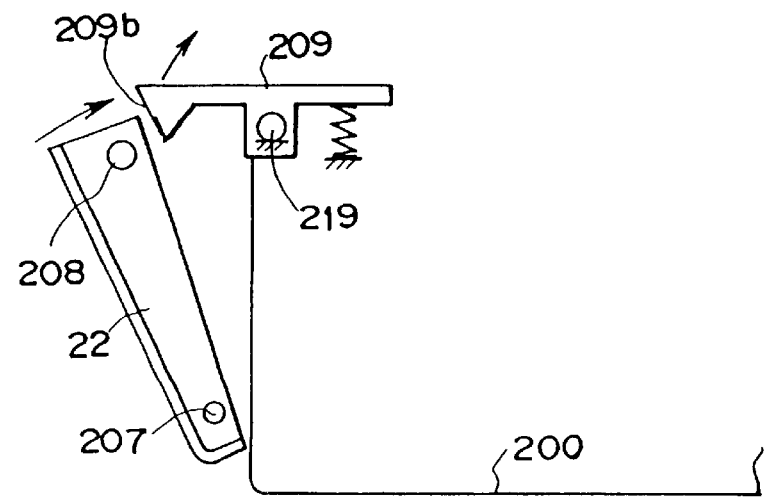

FIGS. 11A to 11C are views for explaining the operation of the lid member 22 and correspond to a sectional view taken along the line of arrows X—X of FIG. 10. Referring to FIGS. 11A to 11C, the lid member 22 can be pivoted by the shafts of left and right axial support members 207 fixed to the main base 200. When the pins 208 are locked by the locking members 209, as shown in FIG. 11A, the lid member 22 is maintained at the closed position. Each locking member 209 can be pivoted by the shaft 219 as the pivot shaft, and has a compression spring 220 on its other end, to maintain the locked state shown in FIG. 11A. Referring to FIG. 11B, when the lid member 22 is opened to the front side, the compression springs 220 are compressed, and the pawls of the locking members 209 ride over the pins 208, as shown in FIG. 11B. Thus, the locked state is canceled, and the lid member 22 is opened to the front side to achieve the state shown in FIG. 10.

As shown in FIG. 11C, when the lid member 22 is manually moved in the direction of arrow, the pins 208 abut against tilt surfaces 209b of the locking members 209. When the lid member 22 is further moved, the pins 208 ride over the pawls of the locking members 209. Thus, the state shown in FIG. 11A is obtained, and the door sensor 210 detects that the lid member 22 is closed.

When the lid member 22 is formed in the above manner, with the cassette being loaded, all the operations are stopped except in a state wherein the lid member 22 is closed, and entry of a foreign substance is prevented, thereby preventing an unanticipated accident.

Referring back to FIG. 10, the cassette mounting portion 21 has an elevating member 222 made of an aluminum plate. Left and right cassette locking pawl members 211 are integrally fixed to the corners of the elevating member 222 through a shaft 223 indicated by a broken line. The shaft 223 is pivotally formed on the elevating member 222. A cassette button 212 is provided below the left cassette locking pawl member 211. When the cassette button 212 is pressed, the left and right cassette locking pawl members 211 are driven to the cancel positions simultaneously.

FIG. 12 is a stereoscopic exploded view of the left and right cassette locking pawl members 211 formed on the elevating member 222. As shown in FIG. 12, the left and right cassette locking pawl members 211 are integrally fixed to the shaft 223, and are formed on the elevating member 222 to be pivotal in the directions of arrows. A compression coil spring 224 is fitted on the cassette button 212, and normally biases the left and right cassette locking pawl members 211 to the locking positions.

Referring back to FIG. 10, three cam shafts 256 that make up the clamp means 11, and stepping motors 253, 254, and 255 for separately driving the cam shafts 256 are fixed on the sub-base 201 at positions shown in FIG. 10. A switching valve 106, a vacuum pump 250, an air pressure generator 104, and a reserve tank serving as a vacuum pressure generator 105 are formed on the sub-base 201 at positions shown in FIG. 10.

An attaching member 216 is fixed over the upper surface of the sub-base 201. The attaching member 216 supports- and fixes upper and lower control boards 214 and 215 as shown in FIG. 10.

Figure 13:
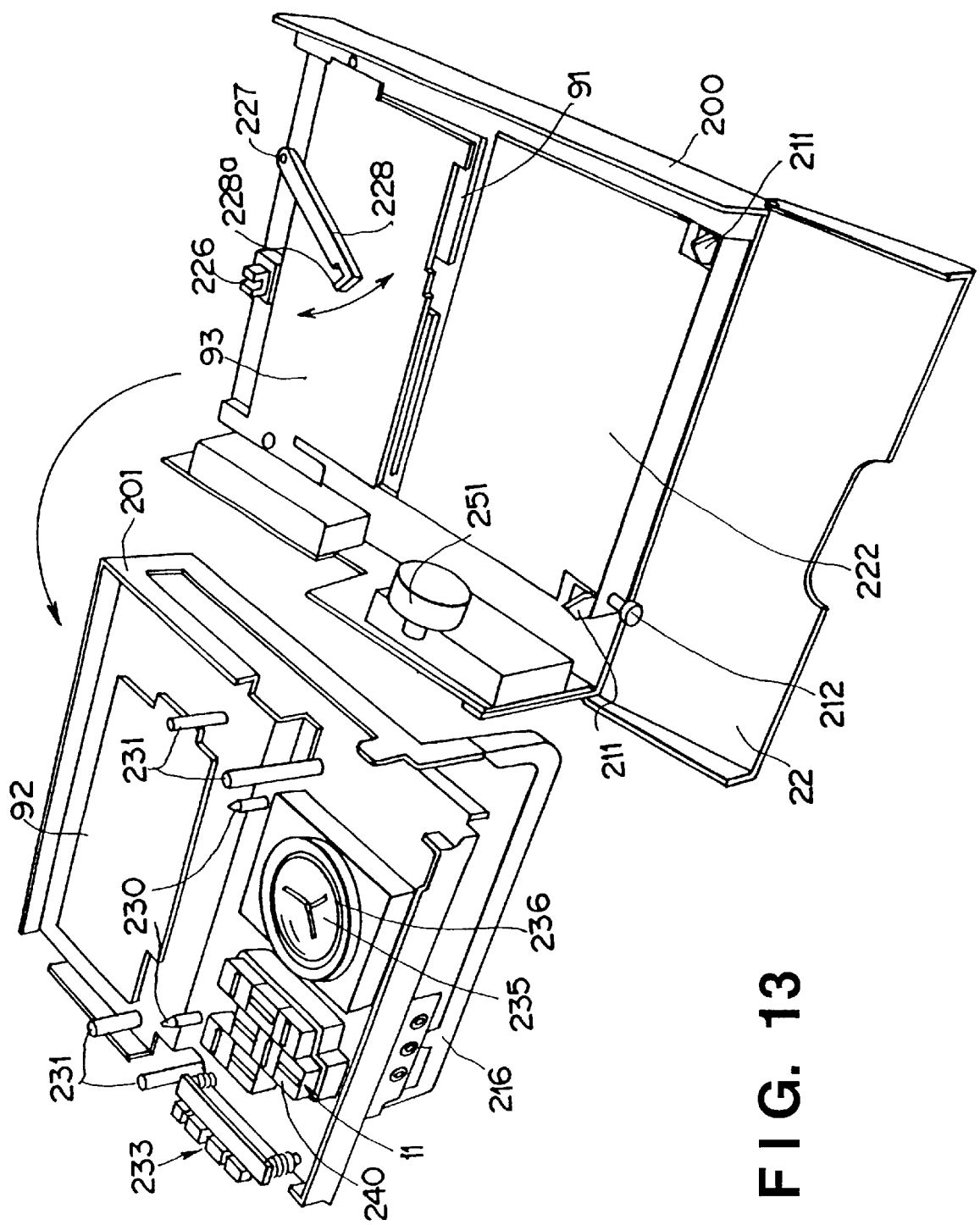
FIG. 13 is an outer appearance perspective view showing a state wherein a main base 200 and sub-base 201 are separated from each other at a separation surface H described with reference to FIG. 10 and the sub-base 201 is reversed.

FIG. 13 is an outer appearance perspective view showing a state wherein the main base 200 and sub-base 201 are separated from each other at the separation surface H described with reference to FIG. 10 and the sub-base 201 is reversed. In FIG. 13, constituent components that have already been described are denoted by the same reference numerals, and a detailed description thereof will be omitted. An elevating motor 251, serving as a stepping motor for driving the elevating member 222 formed on the main base 200, is fixed at the indicated position. The lower and intermediate sheet heaters 91 and 93 are arranged deep behind the elevating member 222. A cassette eject lever 228 is arranged above the intermediate sheet heater 93. The cassette eject lever 228 is pivoted about a lever shaft 227 as the pivot center in the directions indicated by arrows, and is biased by a torsion spring (not shown) to the position shown in FIG. 13. The cassette eject lever 228 has an actuator 228a, at its distal end, for blocking the optical axis of a cassette presence/absence sensor 226, thereby turning on the sensor 226.

Figure 14A:
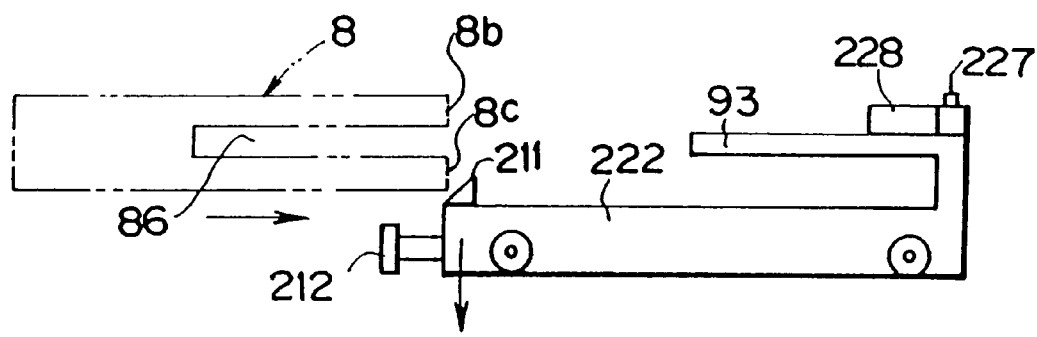
FIGS. 14A, 14B, and 14C are views for explaining the operation of a locking mechanism for the cassette 8.
Figure 14B:
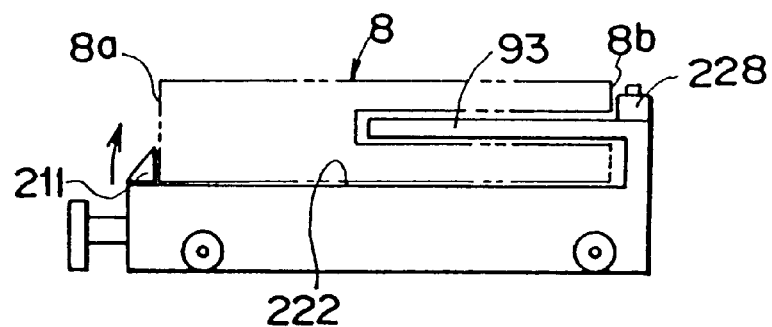
Figure 14C:
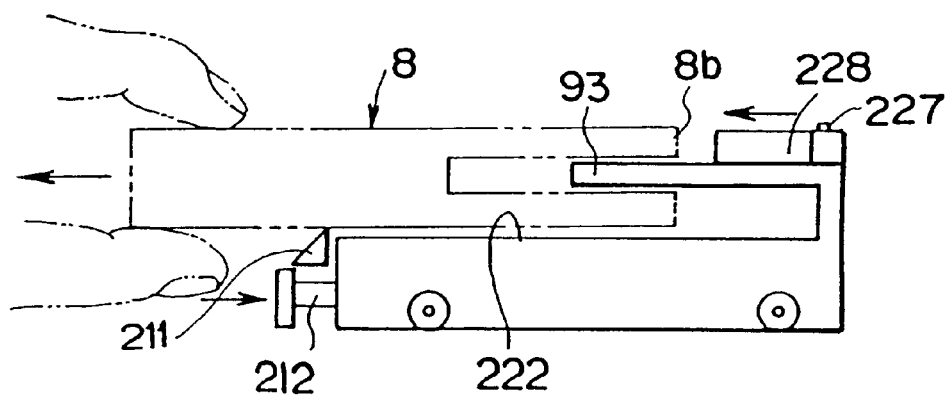

With the above arrangement, in the operation explaining views of FIGS. 14A to 14C, when the cassette 8 indicated by an alternate long and two short dashed line is to be loaded in the direction of arrow and set on the elevating member 222, a cassette leading end face 8c abuts against the left and right cassette locking pawl members 211. The cassette locking pawl members 211 are retracted in the direction of arrow to allow insertion of the cassette 8. When the cassette 8 is further inserted, its gap 86 fits the intermediate sheet heater 93. When the cassette 8 is further pushed forward, a cassette leading end face 8b abuts against the cassette eject lever 228, as shown in FIG. 14B, and moves to turn on the sensor, while a force necessary for ejecting the cassette 8 is accumulated. About that time, the left and right cassette locking pawl members 211 are restored to the positions shown in FIG. 14B to lock a cassette trailing end face 8a. Loading of the cassette 8 onto the elevating member 222 is thus ended.

After dialysis is ended, when the cassette 8 is to be taken out, the cassette button 212 is pressed so the left and right cassette locking pawl members 211 move downward to unlock the cassette trailing end face 8a, and the cassette 8 is ejected to the outside by the operation of the ejecting force accumulated in the cassette eject lever 228.

As described above, when the elevating member 222 is located at the lower position, the cassette 8 can be loaded and ejected.

Referring back to FIG. 13, the upper sheet heater 92, four studs 231 made of a resin, two positioning pins 230 made of stainless steel, a pump chamber 235 with an O-ring 236 around it, eight clampers 240, and a tube clamping means 233 are disposed on the sub-base 201.

Figure 15:
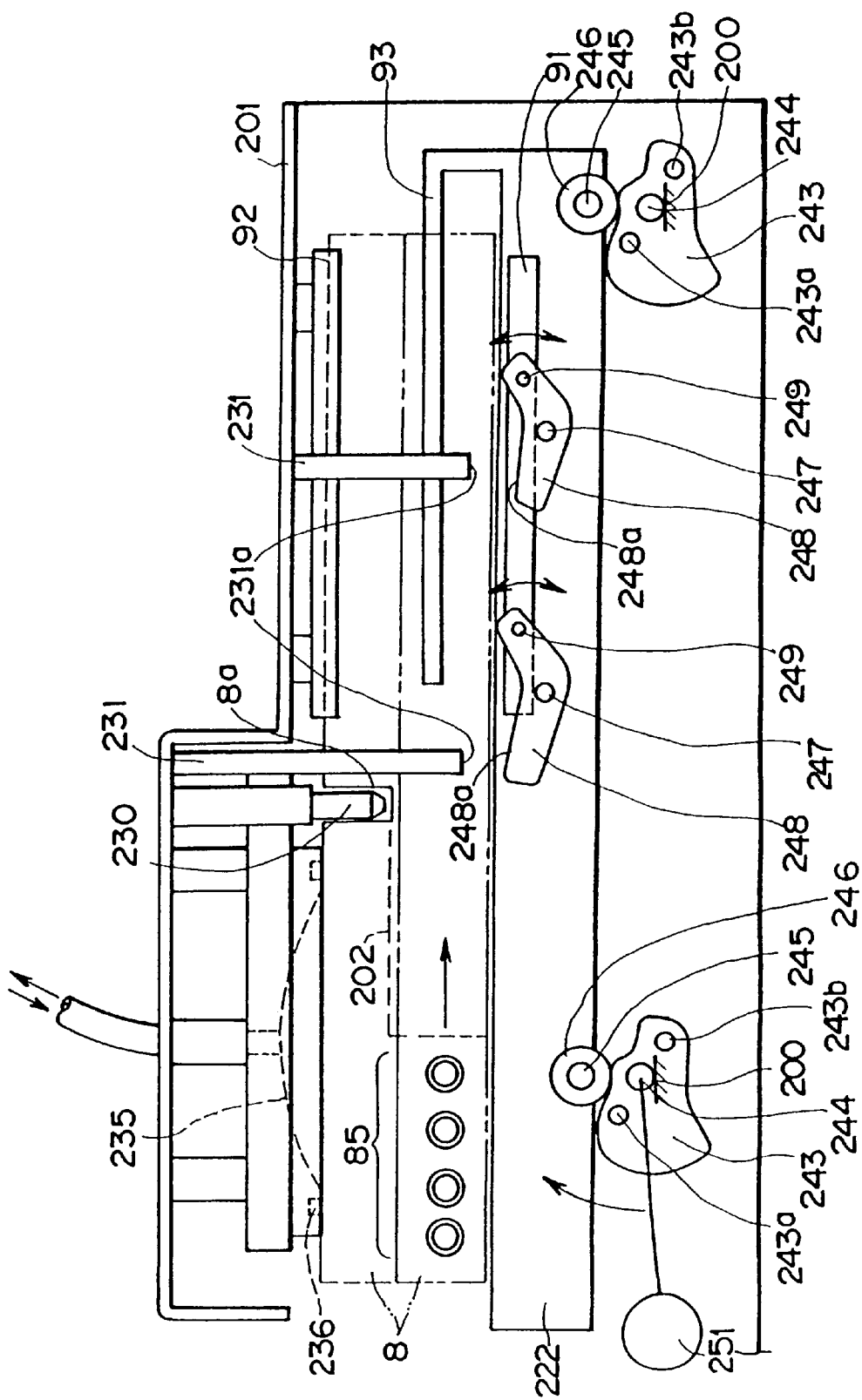
FIG. 15 is a sectional view taken along the line of arrows X—X of FIG. 10.

In the sectional view of FIG. 15 taken along the line of arrows X—X of FIG. 10, each stud 231 has an end face 231*a* that abuts against a second cam member 248 when the elevating member 222 is moved upward.

Cam rollers 246 pivotally axially supported by cam roller shafts 245 are formed on the four corners of the elevating member 222. The cam rollers 246 are supported by the cam surfaces of first cam members 243 fixed to cam shafts 244 axially supported by the main base 200. The first cam members 243 consist of a pair of right and left first cam members 243 on the side shown in FIG. 15 and another pair of right and left first cam members on the opposite side (not shown). When only the first cam members 243 on one side are driven by the motor 251, the first cam members 243 on the other side are driven in synchronism. For this purpose, each first cam member 243 has axial supports 243*a* and 243*b* on its side surface. The axial supports 243*a* and 243*b* are pivotally connected to link members 242 as shown in the side view of FIG. 16. The link members 242 extend from a hole 200*a* formed in the main base 200, and are fixed to the first cam members 243, as shown in FIG. 16.

Shafts 247 are fixed to the two side surfaces of the elevating member 222, and the four second cam members 248 are pivotally, axially supported by the shafts 247, thereby forming a so-called parallel link mechanism in which the aluminum plate of the lower sheet heater 91 is supported by axial supports 249 of the second cam members 248.

The intermediate sheet heater 93 is fixed to the elevating member 222 in a cantilevered manner. When the cassette 8 is inserted at the position indicated by the alternate long and two short dashed line, the positioning pins 230 are not inserted in corresponding holes 8*a*. When the cassette 8 is moved to the position indicated by the broken line, the positioning pins 230 fit in the corresponding holes 8*a*, thereby maintaining the cassette 8 immobile. When the cassette 8 is moved to the position indicated by the broken line, the pump chamber 235 maintains the diaphragm pump 87 airtight.

Figure 16:
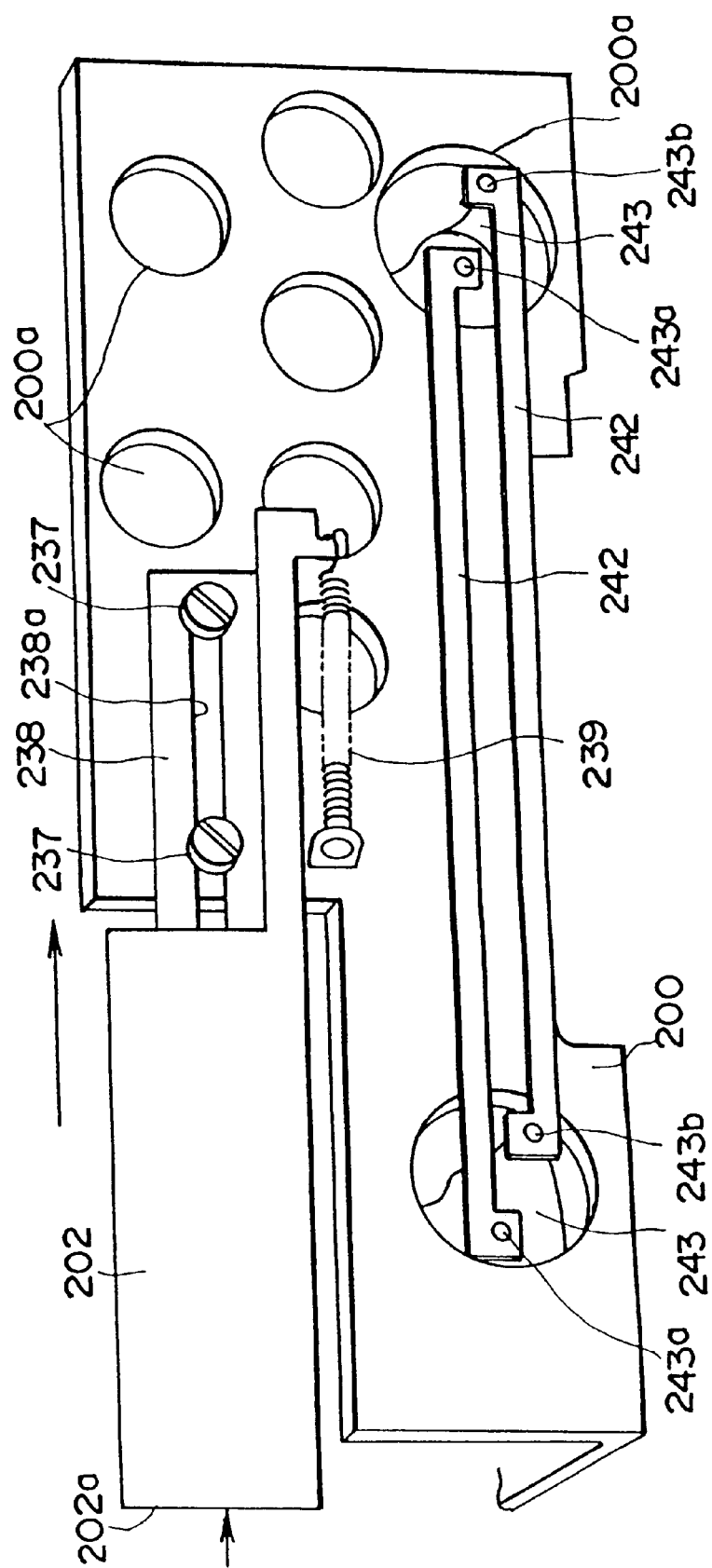
FIG. 16 is a right side view of the dialysis apparatus body.

A guide member 238, a groove 238*a* of which is guided by two flat screws 237 fixed to the main base 200, extends from the blocking plate 202, as shown in FIG. 16. When the cassette 8 is not inserted, the blocking plate 202 is moved to the position shown in FIG. 16 by a tensile force produced by a tension spring 239. When the cassette 8 is inserted, an end 202*a* of the blocking plate 202 abuts against the connection tube, so the blocking plate 202 moves in the direction of arrow.

Figure 17A:
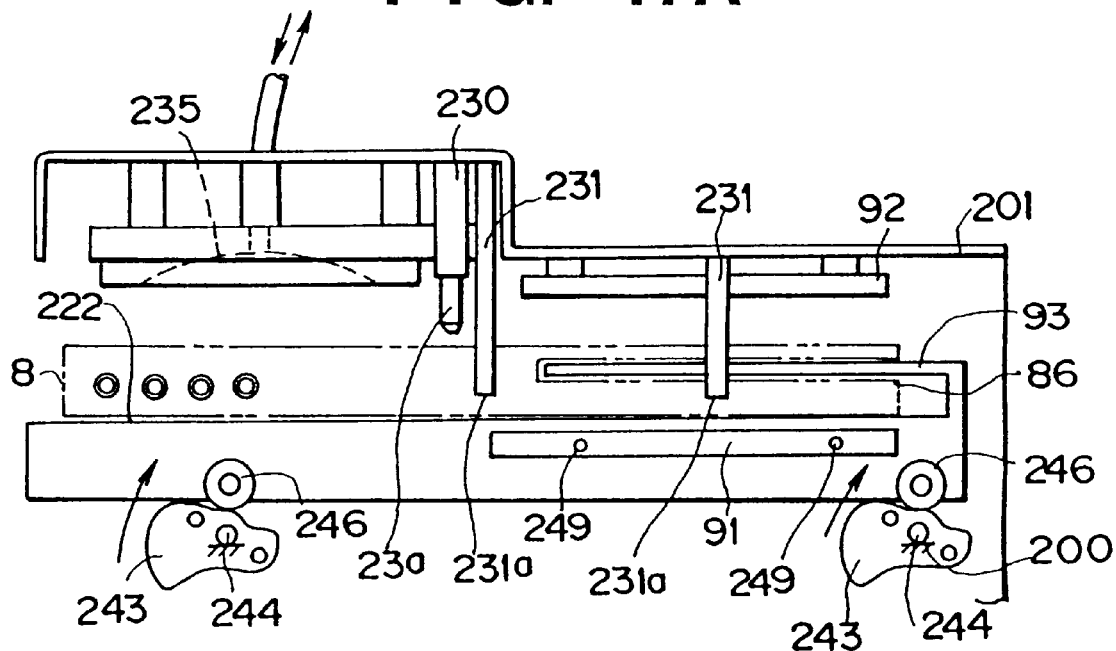
FIGS. 17A and 17B are views for explaining the operation of a cassette loading means.
Figure 17B:
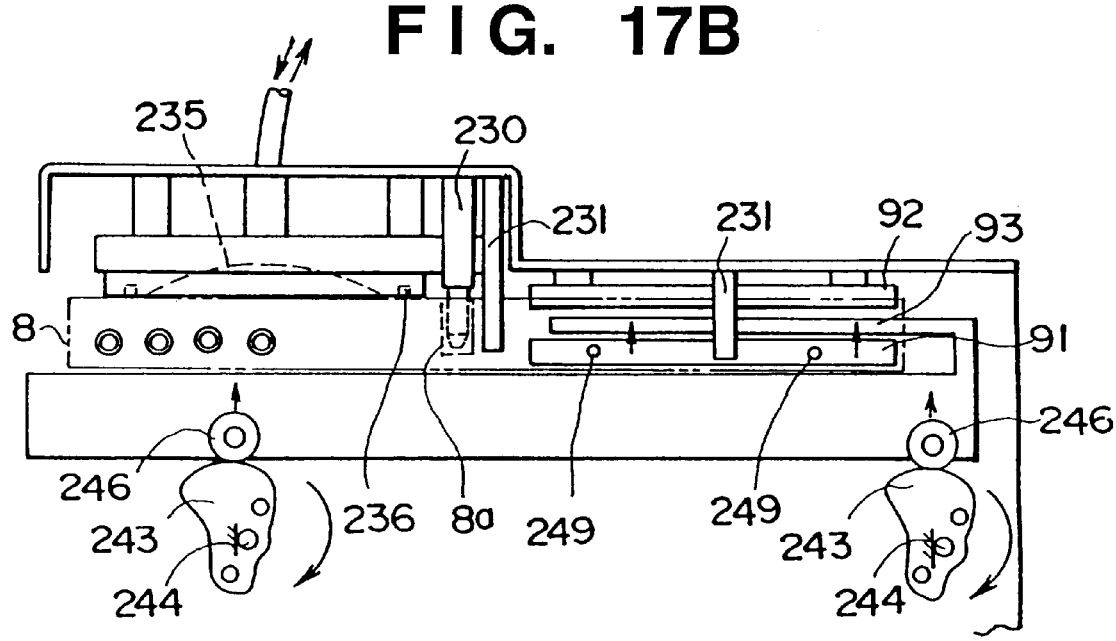

With the above arrangement, in the operation explaining views of FIGS. 17A and 17B, the elevating member 222 has moved to the lower position. When the cassette 8 indicated by the alternate long and two shirt dashed line is set as shown in FIG. 17A, the intermediate sheet heater 93 enters the gap 86.

Then, when the motor is started, the first cam members 243 are pivoted in the directions of arrows, and the cam rollers 246 on the cam surfaces of the first cam members 243 move upward, as shown in FIG. 17B, so that the upper sheet heater 92 and pump chamber 235 come into contact with each other. About that time, when the second cam members 248 abut against the studs 231, the lower sheet heater 91 pivots, so that it moves upward above the axial supports 249 of the second cam members 248, thereby moving the lower sheet heater 91 to the position shown in FIG. 17B.

In the above manner, the respective heaters are maintained in contact with the divisional cassette heating circuits 831 and 832. When the cassette 8 is to be taken out, it moves in the opposite direction to achieve the state shown in FIG. 17A.

Figure 18:
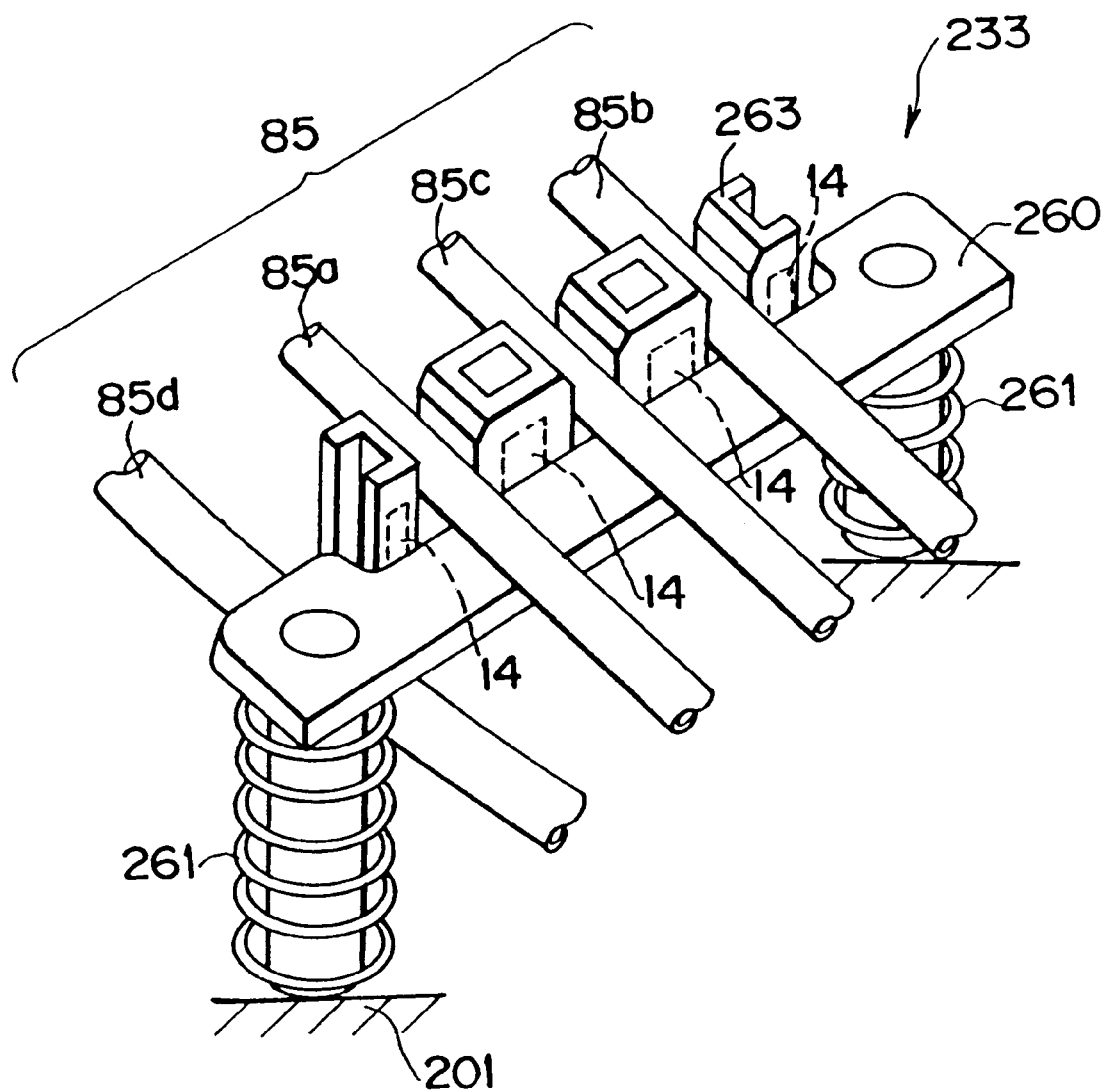
FIG. 18 is an outer appearance perspective view of a tube clamping means 233.

In the state shown in FIG. 17B, as shown in the outer appearance perspective view of FIG. 18 of the tube clamping means 233, the connection tubes 85 are clamped between clamping members 263 incorporating the bubble sensors 14 indicated by broken lines, so that bubbles are detected reliably.

At this time, a press member 260, which is vertically movable on the sub-base 201 because of two compression springs 261, as shown in FIG. 18, moves, and the connection tubes 85 are clamped between the clamping members 263. Since the compression springs 261 are compressed, when the cassette 8 moves to the position shown in FIG. 17A, the press member 260 is pushed by the restoration force of the compression springs 261, and the clamped connection tubes 85 are released.

Figure 19:
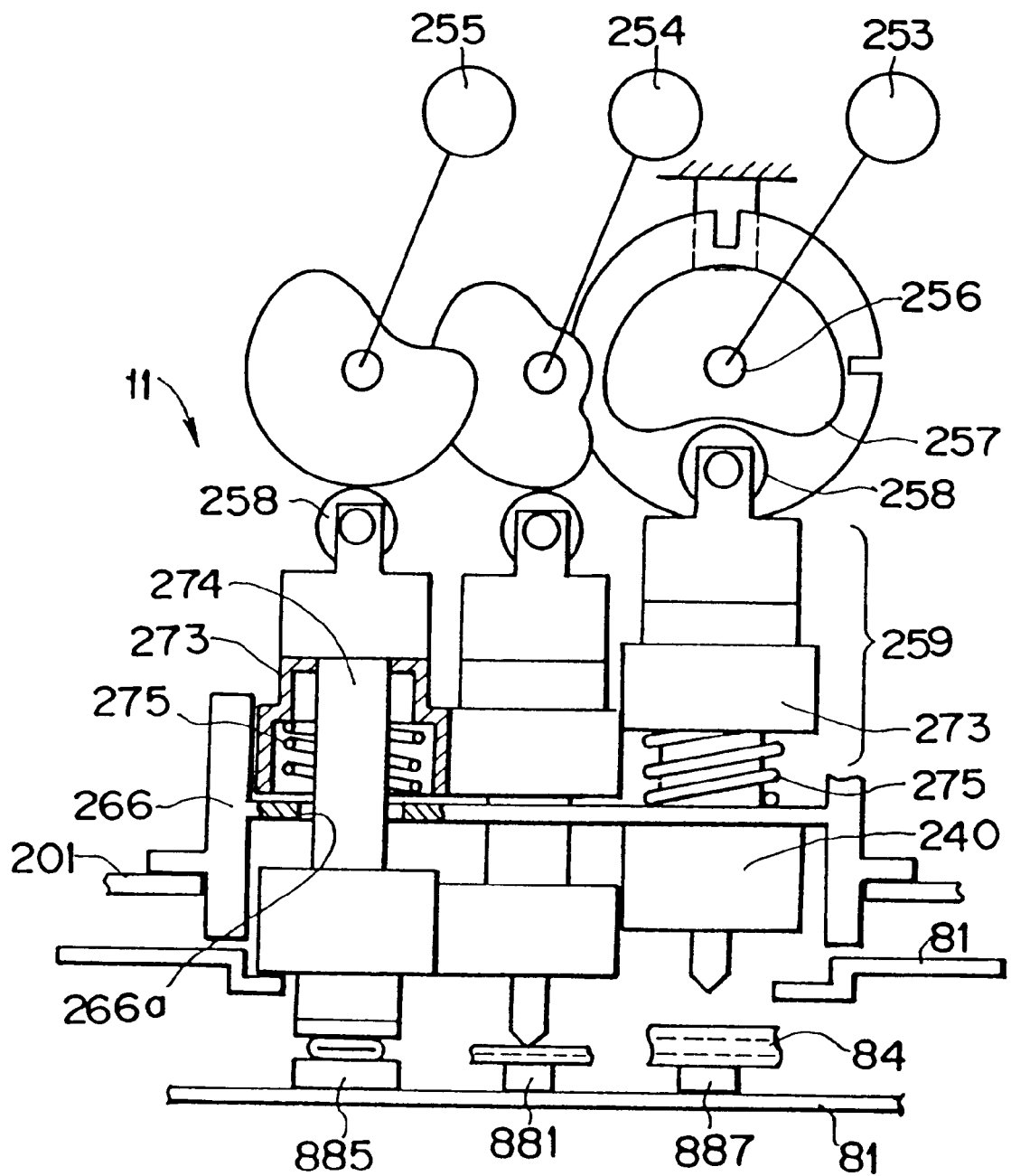
FIG. 19 is a front view of a clamp means 11.

FIG. 19 is a front view of the clamp means 11. Referring to FIG. 19, constituent components that have already been described are denoted by the same reference numerals, and a detailed description thereof will be omitted. The clampers 240 for closing the bypass circuit 84 of the cassette 8 are fixed to the ends of cam assemblies 259 having cam followers 258 which abut against the cam surfaces of cam members 257 separately driven by the motors 253, 254, and 255.

Each cam assembly 259 is formed by inserting a central member 274 in a hole 266*a* formed in a clamper base 266 fixed to the sub-base 201, and placing a restoring large-diameter coil spring 275 in a cap member 273. Thus, each cam assembly 259 is completed such that its cam follower 258 abuts against the cam surface of the cam member 257.

Figure 20:
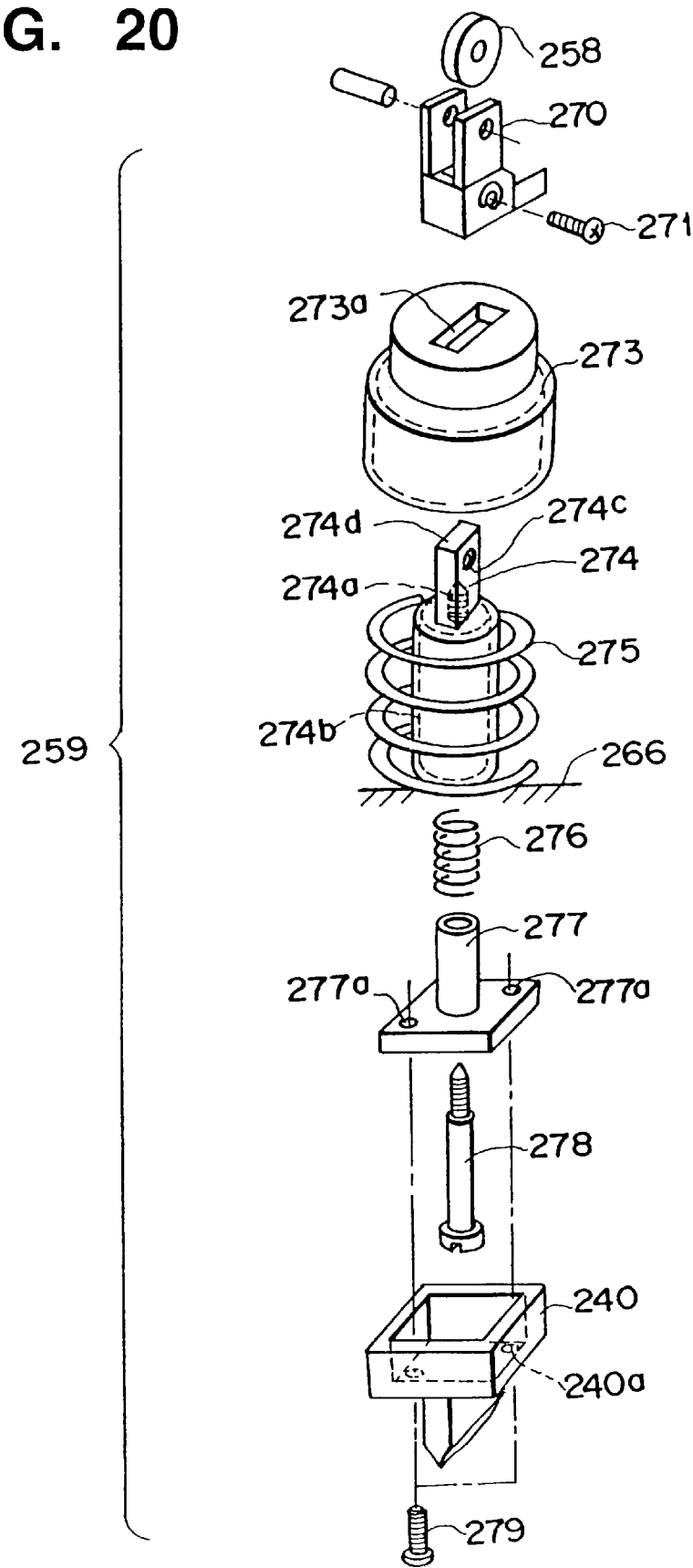
FIG. 20 is a stereoscopic exploded view of a cam assembly 259.

FIG. 20 is a stereoscopic exploded view of each cam assembly 259. Referring to FIG. 20, a bottomed hole 274*b* indicated by a broken line is formed in the central member 274, and a female threaded hole 274*a* is formed in the bottom surface of the bottomed hole 274*b*. A rectangular hole 273*a* is formed in the cap member 273. After a shaper 274*d* of the central member 274 is inserted in the rectangular hole 273*a*, an axial support 270 axially supporting the cam follower 258 is placed over the shaper 274*d*, and is threadably connected to a female threaded portion 274*c* of the central member 274 with a screw 271.

A small-diameter coil spring 276 is set in the bottomed hole 274*b* of the central member 274. Thereafter, a lid member 277 is inserted in the bottomed hole 274*b*, and a long screw 278 is threadably engaged with the female threaded hole 274*a*, so that the lid member 277 is fixed through the small-diameter coil spring 276. Finally, screws 279 are inserted in holes 240*a* formed in the clamper 240, and are threadably engaged with female threaded portions 277*a* of the lid member 277, thereby completing the cam assembly 259. With the above arrangement, in FIG. 19, usually, each cam assembly 259 is vertically driven along the cam surface. When an excessive load is applied, the small-diameter coil spring 276 is compressed, so the flow path is prevented from being closed excessively.

Figure 21:
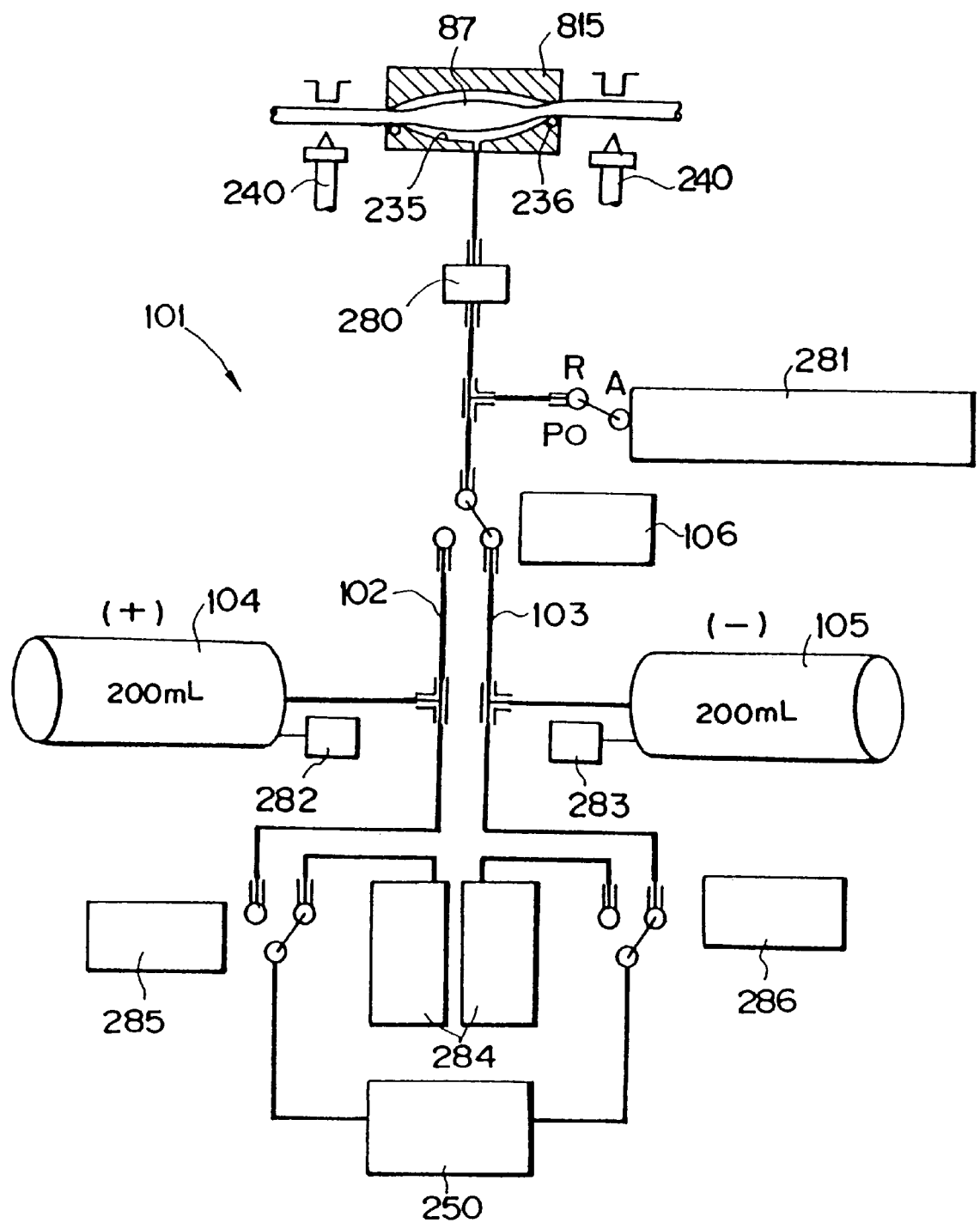
FIG. 21 is a view showing pipes in a pumping actuating means 10 for actuating a diaphragm pump 87.

FIG. 21 is a view showing pipes in the pumping actuating means 10 connected to the pump chamber 235 in order to drive the diaphragm pump 87 provided to the sub-base 201 of the dialysis apparatus body 2.

Referring to FIG. 21, an air circuit (air pressure increasing/reducing circuit) 101 is formed in the dialysis apparatus body 2. When the cassette body 81 is mounted on the cassette mounting portion 21, one end of the air circuit 101 communicates with the pump chamber 235. The pump chamber 235 is branch-connected to a pair of branch air circuits 102 and 103, which are switched by the switching valve 106, through a sensor block 280 with a fluid leak detection function and an open-to-air valve 281. The other end of one branch air circuit 102 is connected to the air pressure generator 104 connected to a pressure sensor 282. The other branch air circuit 103 is connected to the vacuum pressure generator (air reducing unit) 105 connected to a pressure sensor 283.

The open ends of the branch air circuits 102 and 103 are connected to valves 285 and 286, respectively, for performing switching operation between the intake or exhaust side of the vacuum pump 250 and corresponding silencers 284.

With the above arrangement, when the switching valve 106 performs switching operation between the pressurized state wherein the air circuit 101 and one branch air circuit 102 communicate with each other and the pressure-reduced state wherein the air circuit 101 and the other branch air circuit 103 communicate with each other, the interior of the pump chamber 235 is pressurized or pressure-reduced, thereby distributing the dialysis fluid through a bellows 87. More specifically, to reduce the pressure in the pump chamber 235 with the pumping actuating means 10, the third and fifth clamps 113 and 115 shown in FIG. 3 are switched to the unclamp state and clamp state, respectively. To pressurize the interior of the pump chamber 235 with the pumping actuating means 10, the third and fifth clamps 113 and 115 are switched to the clamp state and unclamp state, respectively. Thus, the dialysis fluid can be drained from the dialysis catheter 7 toward the drained fluid tank 6.

The amount of distributed fluid can be measured from pressure changes obtained with the pressure sensors 282 and 283.

The present invention is not limited to the arrangement described above, and can naturally be applied to a case wherein the cassette heating circuit is constituted by one system and the cassette is heated from the above and below with heaters.

Efforts are made to realize downsizing and weight reduction, as described above, so home medical treatment can be performed. For this purpose, aluminum materials and lightweight resin materials are used to form the respective components. If the peritoneal dialysis apparatus is to be used in a hospital, the degree of design freedom increases.

As described above, according to the present invention, there is provided a compact, lightweight peritoneal dialysis apparatus using a disposable cassette integrally formed with a diaphragm and heating portion, in which the flow path can be switched quietly and the heating ability is high. In addition, there is also provided a peritoneal dialysis apparatus in which a detachable cassette can be loaded reliably and easily by anyone while a sufficiently high heating ability is maintained.

Operation performed at home or the like by the patient himself will be described in detail. In the following description, constituent components that have already been described are denoted by the same reference numerals, and a detailed description thereof will be omitted.

For example, the display 23 is formed of a touch panel with a liquid crystal (LCD) panel or the like. In response to touch operation of the touch panel, the display 23 displays various types of information necessary for dialysis and indicates the user to operate the apparatus together with a voice guide from a loudspeaker 400a indicated by a solid line in FIG. 9, so that operability and convenience are ensured.

A sensor 16a for detecting that the lid member 22 is closed as indicated by a solid line in FIG. 1, a sensor 16b for detecting that the cassette 8 is loaded, and a bubble sensor 14a for detecting that bubbles are included in the connection tubes 85 connected to the cassette 8 are disposed at positions shown in FIG. 9.

A hook 2a is formed on the cover of the dialysis apparatus body 2 such that it can be accommodated. The tubes are hung on the hook 2a, thus making distribution of the solution reliable.

FIGS. 22 to 27 are views showing a display screen of the display 23 (FIG. 1) which sequentially changes.

In the block diagram of FIG. 9, when the power supply of the apparatus 2 is turned on and the operating portion 24a is pressed, an initial screen 500 showing the manufacture's name of the apparatus is displayed, as shown in FIG. 22, and the screen shifts to a screen 501 displaying in color a guide nurse and sheep (character image). On a screen 502, moving arrows are displayed to indicate that the storage 152 is being initialized. Simultaneously, a message "Perform treatment at bright, clean place. Do wash your hands." is produced as a voice guide in a synthesizer voice from the loudspeaker 400a. Successively, the screen automatically shifts to a screen 503. On this screen, parameters necessary for peritoneal dialysis, e.g., treatment pattern, initial amount of drained fluid, amount of infused fluid, stay time in the peritoneal cavity, number of cycles, final shot amount of infused fluid, whether the final concentration is altered, dialysis time, planned dialysis end time, and total amount of dialysis fluid, are displayed as the previous dialysis data. If the current treatment is to be performed with the previous conditions, the user touches a touch key 506 "NEXT" to advance to the screen of FIG. 23.

Figure 23:
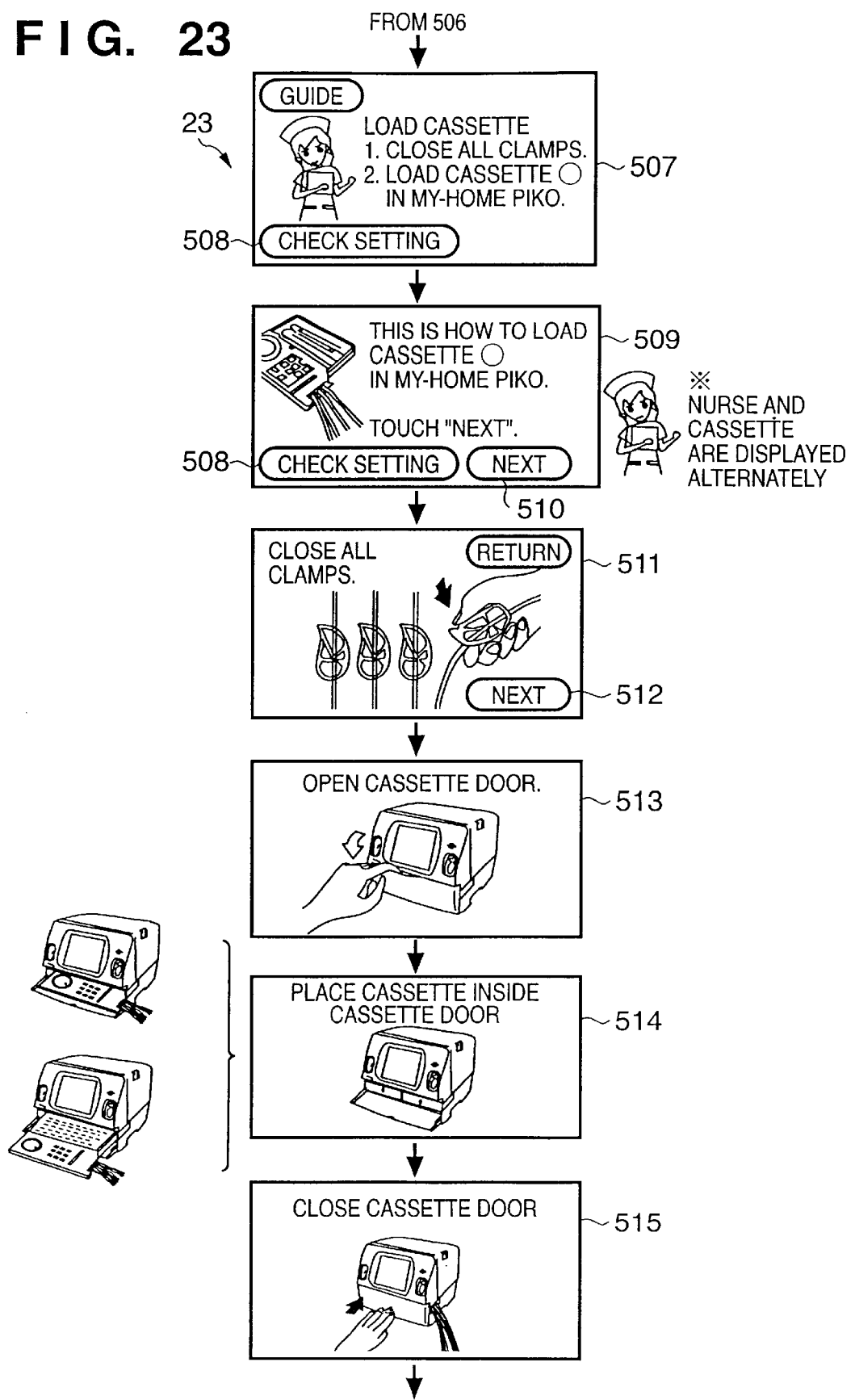
Figure 24:
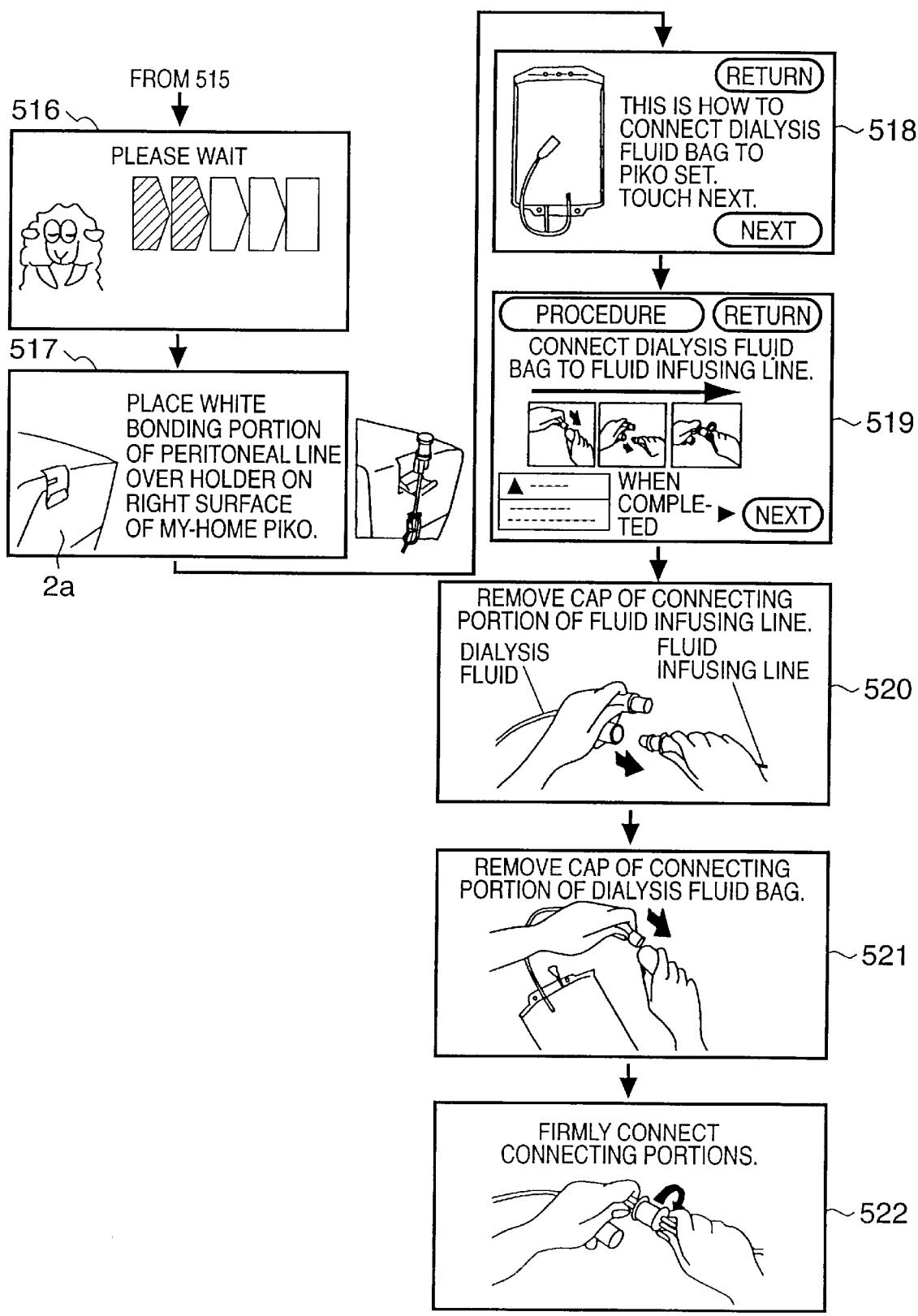

On a screen 507 shown in FIG. 23, a message prompting the user to set the cassette 8 to the mounting portion of the apparatus is displayed together with a voice guide. The screen 507 also displays a touch key 508 "CHECK SETTING" simultaneously. When the user touches the touch key 508, the screen shifts to a screen 523 of FIG. 25. On a screen 509 following the screen 507, a voice guide "This is how to load cassette in my-home piko." is produced while displaying the cassette 8 and the tubes shown in FIG. 22. About that time, a nurse and cassette are displayed alternately. When the patient touches a touch key 510 "NEXT", the screen shifts to a screen 511, and characters "Close all clamps" and a corresponding operation procedure are displayed as a still image in color together with a voice guide. When the user touches a touch key 512 "NEXT" of this screen 511, a screen 513 prompts the user to open the lid member 22 to the front side. A voice guide is produced, and the screen automatically shifts to a screen 514. The screen 514 displays in a color motion image how to insert the cassette 8 through over the lid member of the apparatus. Successively, a screen 515 displays, together with a voice guide, how to close the lid member after the cassette is loaded. The screen then shifts to a screen 516 of FIG. 24, and the user is requested to wait until the cassette is sandwiched with the three heater layers described above. Then, together with a voice guide, a screen 517 prompts the user to set the connection tubes onto the hook 2a of the main body. The screen then shifts to a screen 518.

The screen 518 displays a message "This is how to connect the dialysis fluid bag to piko set (Tradename of Terumo Corporation) 8" together with a voice guide. When the user touches a key "NEXT", the screen shifts to a screen 519, and a voice guide is produced while showing an image indicating how to connect the tube. After this, the screen automatically shifts to screens 520, 521, and 522 to show operation necessary for connection.

The screens of FIG. 25 are the ones that are sequentially displayed when the user touches the touch key 508 "CHECK SETTING" on the screens 507 and 509 of FIG. 23. On a screen 523, a message for prompting the user to check connection is displayed while producing a voice guide. After connection is completed, when the user touches a touch key 524 "NEXT", a screen 525 asking the user to wait is displayed. On a screen 526, unclamp and other procedures necessary after connection are displayed together with a voice guide. On a screen 528, the user touches a touch key "CHECKED", makes preparation for dialysis, and presses the operating portion 24a to start dialysis. On the screen 528, when the user touches touch keys 530 showing upward and downward arrows, items 1 to 5 on the screen are shown as a negative image. Then, the user may touch the touch key "RETURN". This enables checking of the procedures. On the screen 526, the user can select with the touch keys 530 an item for which he needs explanation.

Figure 26:
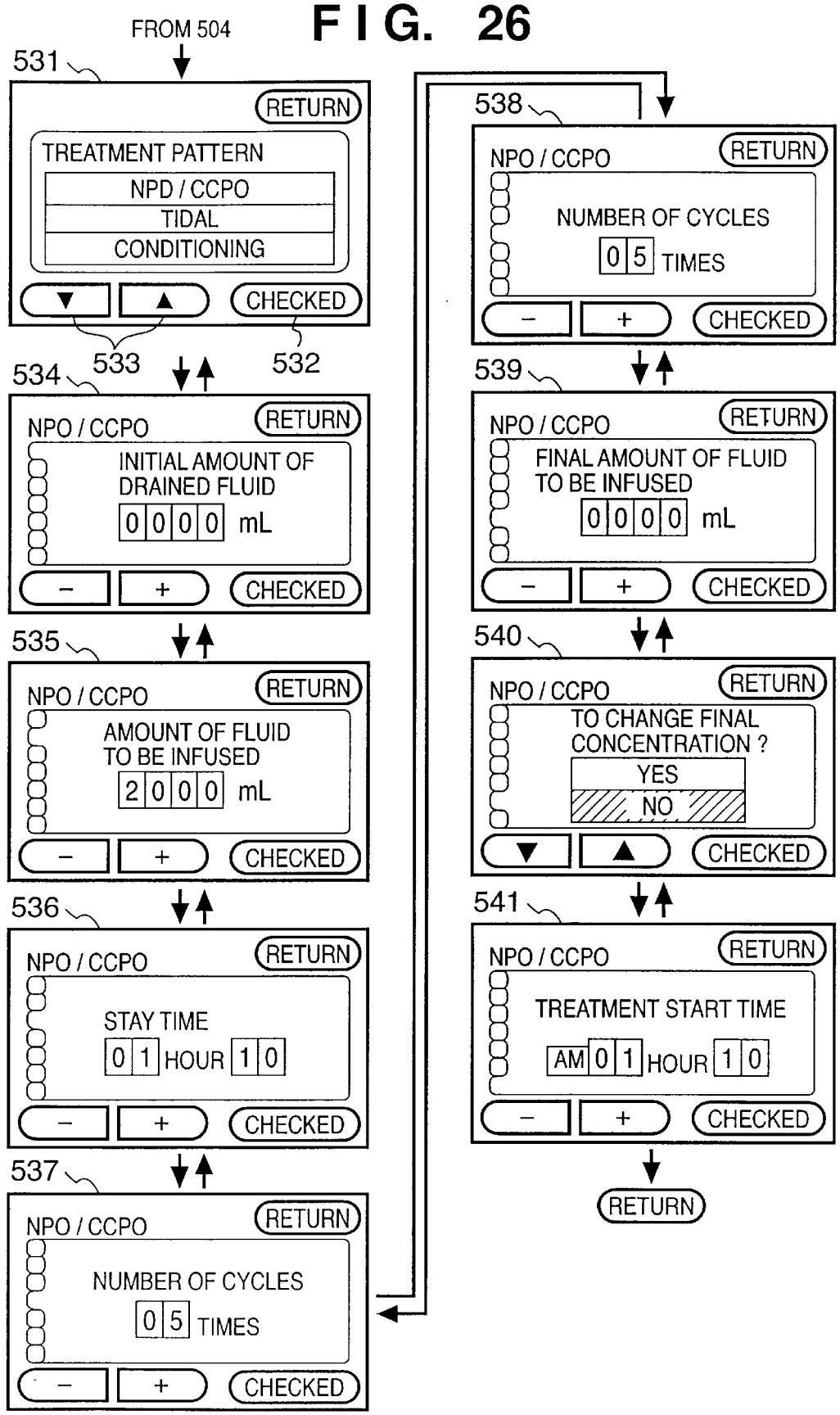

On the screen 503 of FIG. 23, when the user touches a touch key 504 "ALTER", the screen shifts to a screen 531 of FIG. 26. The user is supposed to touch keys 533 showing upward and downward arrows to set conditions through interactive processing with screens 534 to 541. The screens 534 to 541 are monochromatic and their background color does not change. Hence, the patient will know that the preset conditions are being altered.

Contents of abnormal states such as closure of fluid draining line, closure of fluid infusing line, defective fluid infusing, defective fluid draining, insufficient drained fluid amount, closure of additional fluid infusing line, battery voltage decrease, outer temperature decrease, closure of peritoneal line, bubbles detected, power failure, and the like, and operation procedures to cope with them are stored in the storage 152 in advance. If the bubble sensors 14 and various types of sensors 16 detect an abnormality, the screen automatically shifts to screen displaying an abnormal state, and what kind of abnormality has occurred is sequentially displayed. Thus, the user (patient) can sequentially check through questions and answers what countermeasure must be taken.

Figure 27:
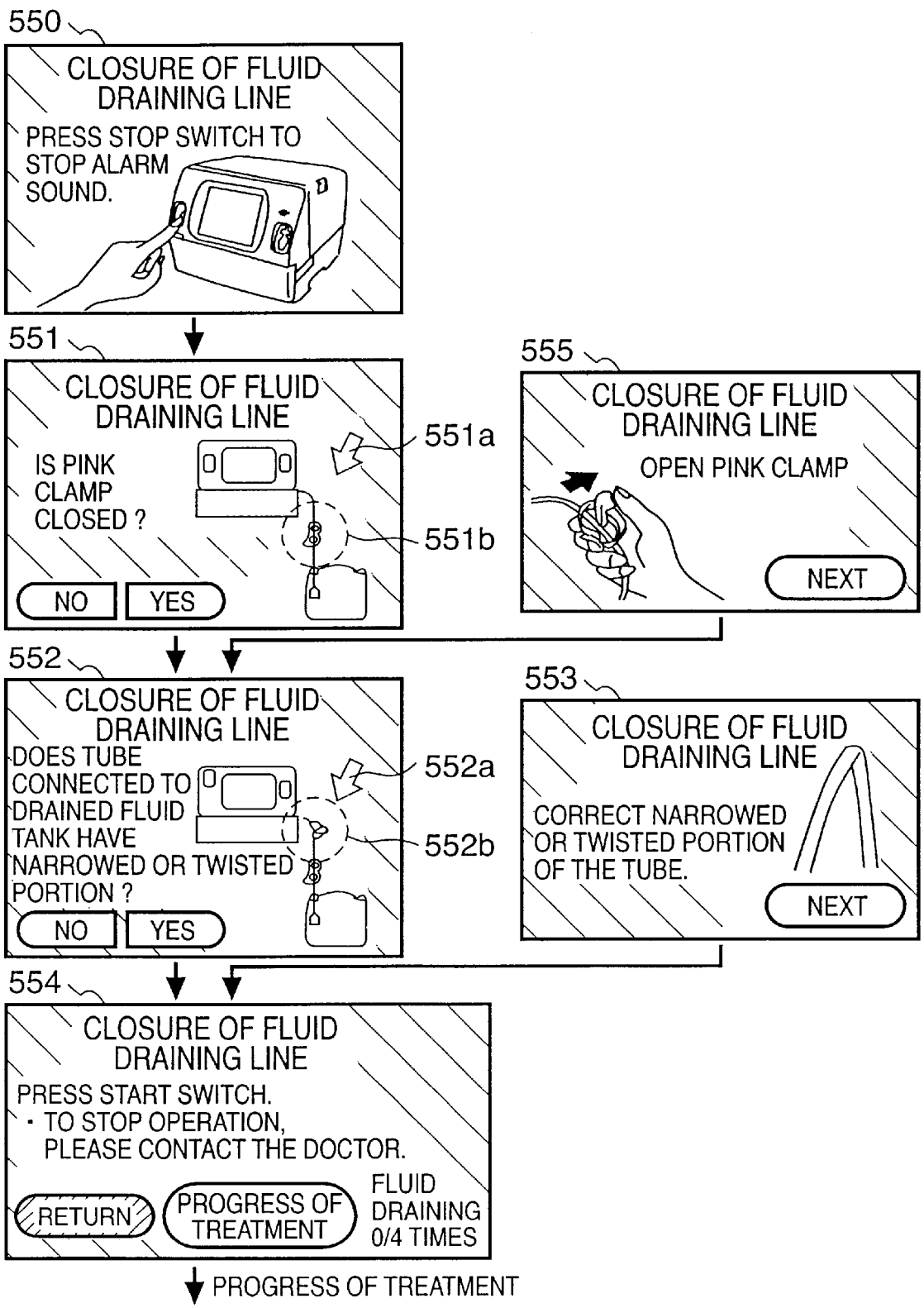

FIG. 27 shows a case wherein the fluid draining line is closed as an example of an abnormal state in dialysis. In order to inform the abnormal state, on screens 550 to 554, messages are displayed as a still image or motion image including characters while producing a voice guide. Simultaneously, the background is displayed in a predetermined prominent color such as yellow or orange indicated by hatched portions, so as to inform the user of the abnormal state.

On the screen 550, characters "Press STOP switch to stop alarm sound." are displayed with an alarm screen, and simultaneously a message "Press STOP switch to stop alarm sound" is produced as a voice guide.

In response to this, when the user presses the operating portion (STOP button) 24b, the screen shifts to a question-and-answer screen as shown on the screen 551. One of closed portions (patterns) stored in the storage 152 in advance is displayed by an arrow 551a and a circular dot mark 551b of a predetermined color (red) together with a diagram of the peritoneal dialysis line, and a question asking "Is pink clamp closed?" is displayed in the form of characters together with a voice guide.

If the user clicks "NO" on the screen 551, the screen shifts to the screen 552. If the user clicks "YES", the screen shifts to a screen 555, and a countermeasure that must be taken is displayed in the form of characters "Open pink clamp" together with a voice guide. When the user performs a necessary procedure following this indication and clicks "NEXT", the screen shifts to the screen 552.

On the screen 552, if the user clicks "NO", the screen shifts to the screen 554. If the user clicks "YES", the screen 555 is displayed, and a countermeasure that must be taken is displayed in the form of characters "Correct narrowed or twisted portion of the tube." together with a voice guide. When the user performs a necessary procedure following this indication and clicks "NEXT", the screen shifts to the screen 554.

On the screen 554, a message "Press START switch. To stop operation, please contact the doctor." is displayed in the form of characters and a voice guide.

In this manner, the contents and locations of abnormalities are assumed and stored in the storage 152 in advance, so the user can sequentially check them.

On the respective screens, if the user presses the operating portion 24a, he can return to the initial operation.

The abnormal states include, in addition to closure of the fluid draining line shown in FIG. 27, closure of fluid infusing line during treatment and priming, defective fluid infusing, defective and insufficient fluid draining, inclusion of bubbles, closure of additional fluid infusing line during treatment and priming, battery backup due to power failure, and outer temperature decrease. Whenever any of these abnormalities occurs, the background color changes to a prominent color such as yellow or orange, and simultaneously the user is informed of the abnormality with a voice guide. Even if a trouble should occur, it can be coped with easily. Therefore, the patient can use the apparatus with confidence.

As has been described above, according to the present invention, automatic dialysis treatment can be performed by the patient himself, and the operation procedures of the apparatus are very clear and easily understood, so treatment can be performed with optimal conditions. Hence, a peritoneal dialysis apparatus can be provided with which even if a trouble should occur, it can be coped with easily, thus allowing peritoneal treatment with optimal conditions.

As many apparently widely different embodiments of the present invention can be made without departing from the spirit and scope thereof, it is to be understood that the invention is not limited to the specific embodiments thereof except as defined in the appended claims.

What is claimed is:

1. A peritoneal dialysis apparatus on which a disposable cassette, integrally formed with a fluid distributing diaphragm, a heating portion and a flow path switching portion, is loaded and which is used by connecting to a dialysis fluid container storing a dialysis fluid and a drained fluid container, comprising:
   a body provided with an operating portion and a display;
   cassette loading means for detachably loading the cassette;
   pumping actuating means for setting the diaphragm in a positive pressure state and negative pressure state, after the cassette is loaded, to distribute the fluid from the dialysis fluid container and to the drained fluid container;

heater means for heating an amount of dialysis fluid to a patient's body temperature while the dialysis fluid stays in the heating portion so that the heating portion is heated from both upper and lower sides after the cassette is loaded;

flow path switching means connected to a plurality of said dialysis fluid containers and which is made of flexible tubes and a plurality of dampers for opening/closing the flow path switching portion in order to form a flow path through which the heated dialysis fluid heated by said heater means is distributed into a peritoneal cavity of a patient and, after a period of time elapses, the dialysis fluid is sucked and drained from the peritoneal cavity; and control means connected to the operating portion, the display, said pumping actuating means, said heater, an said flow path switching means for controlling operation of the operating portion, the display, said pumping actuating means, said heater, and said flow path switching means.

2. The apparatus according to claim 1, wherein an openable/closeable lid for closing an opening of said cassette loading means is disposed on a front surface of said body, and the cassette has, on a side surface thereof, a connection tube to be connected to the dialysis fluid container and the drained fluid container, and a blocking plate is provided which is moved to prevent interference with the connection tube when the cassette is to be loaded through the opening.

3. The apparatus according to claim 2, wherein the body includes a main base and a sub-base, and including clamping canceling means for holding the connection tube in a clamped state with respect to a bubble sensor disposed on the sub-base and for canceling the clamped when the cassette is moved downward from the operative position state of the connection tube.

4. The apparatus according to claim 1, wherein said mounting portion includes and opening in a surface of the body, and including a locking member mounted on the body and adapted to engage a trailing end face of the cassette to set the cassette in a locked state when the cassette is inserted through the opening of said body, and a button connected to the locking member to move the lock member and release engagement of the locking member with the trailing end face of the cassette, and a spring biased lever adapted to abut against a leading end face of the cassette and connected to a sensor for detecting presence and absence of the cassette, the detection of one of the presence and absence of the cassette and ejection of the cassette from a loading position being performed by cooperation of the lever and the locking member.

5. The apparatus according to claim 1, wherein the diaphragm is adapted to be positioned in a pump chamber said pumping actuating means having a switching valve that communicates with the pump chamber to switch the diaphragm between the positive pressure state and the negative pressure state, the pumping actuating means including a vacuum pump connected to the pump chamber, reserve tanks for providing positive and negative pressures, and pressure sensors for detecting pressures in the reserve tanks to monitor a supply amount of the dialysis fluid.

6. The apparatus according to claim 1, including a memory card attachable to and detachable from said body for altering a screen of the display.

7. A peritoneal dialysis apparatus on which a disposable cassette, integrally formed with a fluid distributing diaphragm, a heating portion forming upper and lower systems of flow paths through a gap and a flow path switching portion, is loaded and which is used by connecting to a dialysis fluid container storing a dialysis fluid and a drained fluid container, comprising:

a body provided with a operating portion and a display;

cassette loading means or detachably loading the cassette;

pumping actuating means for setting the diaphragm in a positive pressure state and negative pressure state, after the cassette is mounted, to distribute the fluid from the dialysis fluid container and to the drained fluid container;

heater means having three layers of sheet heaters that come into contact with the upper and lower systems of flow paths in which the dialysis fluid stays to perform heating from above and below, thereby heating an amount of dialysis fluid in the heating portion to a patient's body temperature after the cassette is mounted;

flow path switching means connected to a plurality of said dialysis fluid containers and which is made of flexible tubes and a plurality of dampers for opening/closing the flow path switching portion in order to form a flow path through which the heated dialysis fluid heated by the heater means is distributed into a peritoneal cavity of a patient continuously and, after a period of time elapses, the dialysis fluid is sucked and drained from the peritoneal cavity; and control means connected the operating portion, the display, said cassette loading means, said pumping actuating means, said heater means, and said flow path switching means to control the operating portion, the display, said cassette loading means, said pumping actuating means, and said flow heater means, and said flow path switching means.

8. The apparatus according to claim 7, wherein said plurality of clampers are continuously and intermittently moved by a plurality of cam shafts having a plurality of cams with driving portions of the cam shafts, thereby opening/closing said flow path switching portion.

9. The apparatus according to claim 8, wherein the clampers of said flow path switching means have larger diameter restoring coil springs for abutting the clampers against cam surfaces of the cams, and smaller diameter coil springs preventing a flow path of said flow path switching portion from being closed excessively.

10. The apparatus according to claim 7, wherein the mounting portion includes an opening in a surface of the body through which the cassette is inserted, and including cassette elevating means for vertically moving the cassette after the cassette is inserted through the opening, the cassette being moved from a lower position to an operative position by the cassette elevating means to position the cassette at a predetermined position where each of the upper and lower systems of flow paths come into contact with two of the sheet heaters, said pumping actuating means including a pump chamber that is maintained airtight with respect to the diaphragm, and said flow path switching means is opened/closed by the clampers.

11. The apparatus according to claim 10, wherein said body has a main base and a sub-base fixed to the main base, the three sheet heaters include an upper sheet heater fixed to the sub-base, an intermediate sheet heater adapted to enter the gap of the cassette, and a lower sheet heater, and the cassette elevating means has an elevating member provided on the main base that is vertically movable by a first cam mechanism which is motor-driven, the intermediate sheet heater being fixed in a cantilevered manner on the elevating member, and the lower sheet heater is vertically movable by a second cam mechanism provided on the elevating member, the second cam mechanism serving to abut against a stud extending vertically downward from the sub-base and to be driven pivotally.

12. The apparatus according to claim 11, wherein a pin, which is adapted to be inserted in a positioning hole of the cassette when the cassette is moved upward to the operative position by the cassette elevating means to position the cassette, is disposed vertically on the sub-base.

13. The apparatus according to claim 11, wherein the main base and the sub-base are formed of aluminum plates, and the cassette elevating means is disposed on the main base, and further comprising;

a control board for said control means, power supply means including a battery, the diaphragm being adapted to be positioned in a pump chamber connected to a vacuum pump, and said flow path switching means including clamper driving means disposed on the sub-base.

14. A peritoneal dialysis apparatus having a dialysis fluid circuit including at least one dialysis fluid container filled with a dialysis fluid and at least one drained fluid container for recovering the dialysis fluid, fluid distributing means for distributing the dialysis fluid from the dialysis fluid container as a start point or to the drained fluid container as an end point, display means for informing conditions concerning dialysis, the apparatus configured to supply the dialysis fluid to a patient with the fluid distributing means and to recover a drained fluid and having heater means to perform heating of the dialysis fluid to patient's body temperature, flow path switching means connected to a plurality of said dialysis fluid containers and to the drained fluid container for opening/closing the flow path switching portion in order to form a flow path through which the heated dialysis fluid heated by said heater means is distributed into a peritoneal cavity of a patient and recovering drained dialysis fluid after a predetermined time elapse thereby performing a dialysis, comprising:

an operation procedure necessary for the dialysis is displayed on a display of the display means through a voice guide and at least one of a still image and a motion image including characters.

15. The apparatus according to claim 14, wherein at least one of the still image and the motion image is displayed in color.

16. The apparatus according to claim 14, wherein said display is a liquid crystal touch panel operated by touching, and the operation procedure, as well as an operation for solving an abnormal state and a setting procedure are adapted to be performed by a patient through touching of the panel.

17. The apparatus according to claim 14, comprising a start button for starting the dialysis and a stop button for stopping the dialysis, the start and stop buttons being separately disposed at positions spaced from the display and having different colors, and braille characters positioned under said start and stop buttons.

18. A peritoneal dialysis apparatus having a dialysis fluid circuit including at least one dialysis fluid container filled with a dialysis fluid and at least one drained fluid container for recovering the dialysis fluid, fluid distributing means for distributing the dialysis fluid from the dialysis fluid container as a start point or to the drained fluid container as an end point, display means for informing conditions concerning dialysis, the apparatus configured to supply the dialysis fluid to a patient with the fluid distributing means and to recover a drained fluid, and having heater means to perform heating of the dialysis fluid to a patient's body temperature, flow path switching means connected to a plurality of said dialysis fluid containers and to the drained fluid container for opening/closing a flow path switching portion in order to form a flow path through which the heated dialysis fluid heated by said heater means is distributed into a peritoneal cavity of a patient and recovering drained dialysis fluid after a predetermined time elapse thereby performing a dialysis, comprising:

a color of a background displayed together with a voice guide, in at least one of a still image and a motion image including characters, displayed on the display means being different from a color of a background of the dialysis operation in a normal state.

19. A peritoneal dialysis apparatus having a dialysis fluid circuit including at least one dialysis fluid container filled with a dialysis fluid and at least one drained fluid container for recovering the dialysis fluid, fluid distributing means for distributing the dialysis fluid from the dialysis fluid container as a start point or to the drained fluid container as an end point, display means for informing conditions concerning dialysis, the apparatus configured to supply the dialysis fluid to a patient with the fluid distributing means and to recover a drained fluid, and having heater means to perform heating of the dialysis fluid to a patient's body temperature, flow path switching means connected to a plurality of said dialysis fluid containers and to the drained fluid container for opening/closing a flow path switching portion in order to form a flow path through which the heated dialysis fluid heated by said heater means is distributed into a peritoneal cavity of a patient and recovering drained dialysis fluid after a predetermined time elapse thereby performing a dialysis, comprising:

an operation procedure necessary for the dialysis is displayed on a display of the display means through a voice guide and a still image including characters and with a fixed background color.

* * * * *

UNITED STATES PATENT AND TRADEMARK OFFICE
CERTIFICATE OF CORRECTION

PATENT NO. : 6,595,948 B2
DATED : July 22, 2003
INVENTOR(S) : Minoru Suzuki et al.

It is certified that error appears in the above-identified patent and that said Letters Patent is hereby corrected as shown below:

Column 21,
Line 8, delete "dampers" and insert -- clampers --.
Line 16, delete "an" and insert -- and --.

Column 22,
Line 9, delete "or" insert -- for --.
Line 24, delete "dampers" and insert -- clampers --.

Signed and Sealed this

Thirtieth Day of December, 2003

JAMES E. ROGAN
*Director of the United States Patent and Trademark Office*